US009259565B2

(12) United States Patent
Siopes et al.

(10) Patent No.: US 9,259,565 B2
(45) Date of Patent: *Feb. 16, 2016

(54) MEDICAL VALVE WITH IMPROVED BACK-PRESSURE SEALING

(71) Applicant: NP Medical Inc., Clinton, MA (US)

(72) Inventors: William Siopes, Ayer, MA (US); Luis Maseda, Natick, MA (US); Ian Kimball, Townsend, MA (US)

(73) Assignee: NP Medical Inc., Clinton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/041,660

(22) Filed: Sep. 30, 2013

(65) Prior Publication Data

US 2014/0031765 A1 Jan. 30, 2014

Related U.S. Application Data

(63) Continuation of application No. 12/819,551, filed on Jun. 21, 2010, now Pat. No. 8,568,371.

(60) Provisional application No. 61/219,319, filed on Jun. 22, 2009.

(51) Int. Cl.
*A61M 39/26* (2006.01)

(52) U.S. Cl.
CPC .......... *A61M 39/26* (2013.01); *A61M 2039/268* (2013.01)

(58) Field of Classification Search
CPC ... A61M 39/26; A61M 39/24; A61M 39/228; A61M 25/0606; A61M 2039/263; A61M 2039/2486; A61M 2039/2433; A61M 2039/2473; A61M 39/243

USPC ............. 604/256, 236, 247, 248, 249, 238, 604/167.04, 167.02, 33, 34, 905
See application file for complete search history.

(56) References Cited

U.S. PATENT DOCUMENTS 2,594,405 A 4/1952 Deters ............................ 137/53
2,693,801 A 11/1954 Foreman ...................... 128/214

(Continued)

FOREIGN PATENT DOCUMENTS

EP  0 268 480 A1   5/1988   ............ A61M 25/00
EP  0 629 418 A2  12/1994   ............ A61M 39/04

(Continued)

OTHER PUBLICATIONS

Sylvie Reinbold, Authorized Officer European Patent Office, International Search Report—Application No. PCT/US2010/039333, dated Sep. 14, 2010, together with the Written Opinion of the International Searching Authority (11 pages).

(Continued)

*Primary Examiner* — Nicholas Lucchesi
*Assistant Examiner* — Melissa A Snyder
(74) *Attorney, Agent, or Firm* — Sunstein Kann Murphy & Timbers LLP

(57) ABSTRACT

A medical valve transitions between an open mode that permits fluid flow, and a closed mode that prevents fluid flow. To that end, the medical valve has a housing with an inlet and an outlet, a rigid member movably mounted within the housing, and a resilient member with a sealing portion. The housing also has at least one relief zone that is in fluid communication with the outlet when the valve is in the closed mode. The rigid member may have a proximal end, a distal end, and a flow channel. The relief zone may be radially outward from the sealing portion. The sealing portion may seal the valve and prevent fluid from passing through the valve when in the closed mode.

19 Claims, 14 Drawing Sheets

(56) References Cited

U.S. PATENT DOCUMENTS

| | | | |
|---|---|---|---|
| 2,705,501 A | 4/1955 | Fritzsch et al. | 137/112 |
| 2,756,740 A | 7/1956 | Deane | 128/1 |
| 2,899,975 A | 8/1959 | Fernandez | 137/543.17 |
| 2,919,935 A | 1/1960 | Nyberg | 284/18 |
| 2,999,499 A | 9/1961 | Willet | 128/214 |
| 3,087,492 A | 4/1963 | Garth et al. | 128/350 |
| 3,105,511 A | 10/1963 | Murphy, Jr. | 137/399 |
| 3,192,949 A | 7/1965 | De See | 137/540 |
| 3,279,497 A | 10/1966 | Norton et al. | 137/614.03 |
| 3,385,301 A | 5/1968 | Harautuncian | 128/349 |
| 3,399,677 A | 9/1968 | Gould et al. | 128/349 |
| 3,416,567 A | 12/1968 | von Dardel et al. | 137/604 |
| 3,423,063 A | 1/1969 | German | 251/149.6 |
| 3,506,005 A | 4/1970 | Gilio et al. | 128/214 |
| 3,538,950 A | 11/1970 | Porteners | 137/608 |
| 3,570,484 A | 3/1971 | Steer et al. | 128/214 |
| 3,572,375 A | 3/1971 | Rosenberg | 137/512 |
| 3,618,892 A | 11/1971 | Sciuto, Jr. | 251/149.2 |
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,838,843 A | 10/1974 | Bernhard | 251/149.1 |
| 3,921,656 A | 11/1975 | Meisenheimer, Jr. et al. | 137/68 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,181,149 A | 1/1980 | Cox | 137/614.02 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,335,747 A | 6/1982 | Mitsumoto et al. | 137/614.06 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,445,664 A | 5/1984 | Allread | 251/149.2 |
| 4,458,480 A | 7/1984 | Irwin | 60/39.63 |
| 4,473,211 A | 9/1984 | Fremy | 251/149.2 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,627,598 A | 12/1986 | Fremy | 251/149.2 |
| 4,661,110 A | 4/1987 | Fortier et al. | 604/256 |
| 4,664,149 A | 5/1987 | Fremy | 137/614.06 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329.1 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,830,331 A | 5/1989 | Vindum | 251/63 |
| 4,842,591 A | 6/1989 | Luther | 604/283 |
| 4,850,978 A | 7/1989 | Dudar et al. | 604/201 |
| 4,874,377 A | 10/1989 | Newgard et al. | 604/167 |
| 4,905,965 A | 3/1990 | Dolev | 251/149.9 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,944,329 A | 7/1990 | Cardin et al. | 137/614.05 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,050,841 A | 9/1991 | Jacobsson | 251/149.9 |
| 5,059,175 A | 10/1991 | Hanover et al. | 604/891.1 |
| 5,065,783 A | 11/1991 | Ogle, II | 137/68.1 |
| 5,080,654 A | 1/1992 | Picha et al. | 604/167 |
| 5,085,645 A | 2/1992 | Purdy et al. | 604/167 |
| 5,098,394 A | 3/1992 | Luther | 604/167 |
| 5,100,394 A | 3/1992 | Dudar et al. | 604/283 |
| 5,108,380 A | 4/1992 | Herlitze et al. | 604/283 |
| 5,122,123 A | 6/1992 | Vaillancourt | 604/192 |
| 5,147,333 A | 9/1992 | Raines | 604/249 |
| 5,163,922 A | 11/1992 | McElveen, Jr. et al. | 604/249 |
| 5,171,230 A | 12/1992 | Eland et al. | 604/250 |
| 5,184,652 A | 2/1993 | Fan | 141/21 |
| 5,190,067 A | 3/1993 | Paradis et al. | 137/1 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A * | 12/1993 | Thomas et al. | 604/539 |
| 5,280,876 A | 1/1994 | Atkins | 251/149.1 |
| 5,289,849 A | 3/1994 | Paradis | 137/606 |
| 5,295,657 A | 3/1994 | Atkinson | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,342,315 A | 8/1994 | Rowe et al. | 604/167 |
| 5,342,326 A | 8/1994 | Peppel et al. | 604/284 |
| 5,349,984 A | 9/1994 | Weinheimer et al. | 137/543.21 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,397,314 A | 3/1995 | Farley et al. | 604/256 |
| 5,401,255 A | 3/1995 | Sutherland et al. | 604/247 |
| 5,403,284 A | 4/1995 | Gross | 604/167 |
| 5,439,451 A | 8/1995 | Collinson et al. | 604/247 |
| 5,441,487 A | 8/1995 | Vedder | 604/167 |
| 5,456,675 A | 10/1995 | Wolbring et al. | 604/280 |
| 5,458,640 A | 10/1995 | Gerrone | 604/264 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,487,728 A | 1/1996 | Vaillancourt | 604/86 |
| 5,489,274 A | 2/1996 | Chu et al. | 604/167 |
| 5,509,433 A | 4/1996 | Paradis | 137/1 |
| 5,509,912 A * | 4/1996 | Vaillancourt et al. | 604/537 |
| 5,514,116 A | 5/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,535,771 A | 7/1996 | Purdy et al. | 137/15 |
| 5,535,785 A | 7/1996 | Werge et al. | 137/843 |
| 5,540,661 A | 7/1996 | Tomisaka et al. | 604/265 |
| 5,549,566 A | 8/1996 | Elias et al. | 604/167 |
| 5,549,577 A | 8/1996 | Siegel et al. | 604/256 |
| 5,555,908 A | 9/1996 | Edwards et al. | 137/329.1 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |

(56) References Cited

U.S. PATENT DOCUMENTS

| | | | | |
|---|---|---|---|---|
| 5,613,663 | A | 3/1997 | Schmidt et al. | 251/149.2 |
| 5,616,129 | A | 4/1997 | Mayer | 604/167 |
| 5,616,130 | A | 4/1997 | Mayer | 604/167 |
| 5,620,434 | A | 4/1997 | Brony | 604/406 |
| 5,628,732 | A | 5/1997 | Antoon, Jr. et al. | 604/167 |
| 5,674,206 | A | 10/1997 | Allton et al. | 604/249 |
| 5,676,346 | A | 10/1997 | Leinsing | 251/149.1 |
| 5,685,866 | A | 11/1997 | Lopez | 604/249 |
| 5,694,686 | A | 12/1997 | Lopez | 29/890.126 |
| 5,695,466 | A | 12/1997 | Lopez et al. | 604/93 |
| 5,699,821 | A | 12/1997 | Paradis | 137/1 |
| 5,700,248 | A * | 12/1997 | Lopez | 604/249 |
| 5,730,418 | A | 3/1998 | Feith et al. | 251/149.6 |
| 5,749,861 | A * | 5/1998 | Guala et al. | 604/249 |
| RE35,841 | E | 7/1998 | Frank et al. | 604/256 |
| 5,775,671 | A | 7/1998 | Cote, Sr. | 251/149.8 |
| 5,776,113 | A | 7/1998 | Daugherty et al. | 604/280 |
| 5,782,816 | A | 7/1998 | Werschmidt et al. | 604/256 |
| 5,788,215 | A | 8/1998 | Ryan | 251/149.6 |
| 5,806,551 | A | 9/1998 | Meloul et al. | 137/15 |
| 5,806,831 | A | 9/1998 | Paradis | 251/149.1 |
| 5,817,069 | A | 10/1998 | Arnett | 604/256 |
| 5,820,601 | A | 10/1998 | Mayer | 604/167 |
| 5,836,923 | A | 11/1998 | Mayer | 604/246 |
| 5,921,264 | A | 7/1999 | Paradis | 137/15 |
| 5,947,954 | A | 9/1999 | Bonaldo | 604/533 |
| 5,957,898 | A | 9/1999 | Jepson et al. | 604/256 |
| 5,967,490 | A | 10/1999 | Pike | 251/149.1 |
| 6,029,946 | A | 2/2000 | Doyle | 251/149.1 |
| 6,036,171 | A | 3/2000 | Weinheimer et al. | 251/149.1 |
| 6,039,302 | A | 3/2000 | Cote, Sr. et al. | 251/149.1 |
| 6,048,335 | A | 4/2000 | Mayer | 604/167 |
| 6,050,978 | A | 4/2000 | Orr et al. | 604/249 |
| 6,063,062 | A | 5/2000 | Paradis | 604/249 |
| 6,068,011 | A | 5/2000 | Paradis | 137/1 |
| 6,079,432 | A | 6/2000 | Paradis | 137/1 |
| 6,089,539 | A | 7/2000 | Kouda | 251/149.2 |
| 6,089,541 | A | 7/2000 | Weinheimer et al. | 251/149.6 |
| 6,090,074 | A | 7/2000 | Brimhall et al. | 604/167.05 |
| 6,117,114 | A | 9/2000 | Paradis | 604/246 |
| 6,142,446 | A | 11/2000 | Leinsing | 251/149.1 |
| 6,152,900 | A | 11/2000 | Mayer | 604/167 |
| 6,158,458 | A | 12/2000 | Ryan | 137/515.5 |
| 6,183,448 | B1 | 2/2001 | Mayer | 604/256 |
| 6,189,859 | B1 | 2/2001 | Rohrbough et al. | 251/149.1 |
| 6,206,860 | B1 | 3/2001 | Richmond | 604/246 |
| 6,206,861 | B1 | 3/2001 | Mayer | 604/246 |
| 6,221,065 | B1 | 4/2001 | Davis | 604/539 |
| 6,228,069 | B1 | 5/2001 | Barth et al. | 604/249 |
| 6,245,048 | B1 | 6/2001 | Fangrow, Jr. et al. | 604/249 |
| 6,290,206 | B1 | 9/2001 | Doyle | 251/149.1 |
| 6,344,033 | B1 | 2/2002 | Jepson et al. | 604/256 |
| 6,364,869 | B1 | 4/2002 | Bonaldo | 604/537 |
| 6,422,267 | B1 | 7/2002 | Makishima et al. | 137/616.7 |
| 6,428,520 | B1 | 8/2002 | Lopez et al. | 604/249 |
| 6,485,472 | B1 | 11/2002 | Richmond | 604/246 |
| 6,491,668 | B1 | 12/2002 | Paradis | 604/246 |
| 6,541,802 | B2 | 4/2003 | Doyle | 257/149.1 |
| 6,543,745 | B1 | 4/2003 | Enerson | 251/149.7 |
| 6,585,229 | B2 | 7/2003 | Cote, Sr. et al. | 251/149.1 |
| 6,595,964 | B2 | 7/2003 | Finley et al. | 604/246 |
| 6,595,981 | B2 | 7/2003 | Huet | 604/523 |
| 6,598,620 | B1 | 7/2003 | Fremy | 137/614.03 |
| 6,609,696 | B2 | 8/2003 | Enerson | 251/86 |
| 6,669,673 | B2 | 12/2003 | Lopez | 604/249 |
| 6,695,817 | B1 | 2/2004 | Fangrow, Jr. | 604/167.01 |
| 6,706,022 | B1 | 3/2004 | Leinsing et al. | 604/247 |
| 6,745,998 | B2 | 6/2004 | Doyle | 251/149.6 |
| 6,755,391 | B2 | 6/2004 | Newton et al. | 251/149.6 |
| 6,779,777 | B2 | 8/2004 | Kouda | 251/149.6 |
| 6,802,490 | B2 | 10/2004 | Leinsing et al. | 251/149.6 |
| 6,808,161 | B1 | 10/2004 | Hishikawa | 251/149.1 |
| 6,811,139 | B2 | 11/2004 | Hishikawa | 251/149.1 |
| 6,827,329 | B2 | 12/2004 | Mikiya et al. | 251/97 |
| 6,840,501 | B2 | 1/2005 | Doyle | 251/149.1 |
| 6,869,426 | B2 | 3/2005 | Ganem | 604/533 |
| 6,871,838 | B2 | 3/2005 | Raines et al. | 251/149.4 |
| 6,883,778 | B1 | 4/2005 | Newton et al. | 251/149.1 |
| 6,892,998 | B2 | 5/2005 | Newton | 251/149.1 |
| 6,899,132 | B2 | 5/2005 | Mikiya et al. | 137/616.7 |
| 6,916,309 | B2 | 7/2005 | Fangrow, Jr. | 604/167.01 |
| 6,932,795 | B2 | 8/2005 | Lopez et al. | 604/249 |
| 6,964,406 | B2 | 11/2005 | Doyle | 251/149.6 |
| 6,991,215 | B2 | 1/2006 | Kiehne | 251/149.6 |
| 7,004,934 | B2 | 2/2006 | Vaillancourt | 604/533 |
| 7,008,404 | B2 | 3/2006 | Nakajima | 604/158 |
| 7,014,169 | B2 | 3/2006 | Newton et al. | 251/149.6 |
| 7,028,982 | B2 | 4/2006 | Kohda | 251/149.2 |
| 7,037,302 | B2 | 5/2006 | Vaillancourt | 604/533 |
| 7,056,308 | B2 | 6/2006 | Utterberg | 604/256 |
| 7,063,685 | B2 | 6/2006 | Rome | 604/256 |
| 7,070,164 | B2 | 7/2006 | Kohda | 251/149.2 |
| 7,100,890 | B2 | 9/2006 | Cote, Sr. et al. | 251/149.1 |
| 7,104,520 | B2 | 9/2006 | Leinsing et al. | 251/149.6 |
| 7,114,701 | B2 | 10/2006 | Peppel | 251/149 |
| 7,118,560 | B2 | 10/2006 | Bonaldo | 604/537 |
| 7,125,396 | B2 | 10/2006 | Leinsing et al. | 604/167.03 |
| 7,131,458 | B2 | 11/2006 | Kohda | 137/614.03 |
| 7,184,825 | B2 | 2/2007 | Leinsing et al. | 604/20 |
| 7,244,249 | B2 | 7/2007 | Leinsing et al. | 604/500 |
| 7,306,199 | B2 | 12/2007 | Leinsing et al. | 251/149.6 |
| 7,314,061 | B2 | 1/2008 | Peppel | 137/605 |
| 7,329,249 | B2 | 2/2008 | Bonaldo | 604/537 |
| 7,343,931 | B2 | 3/2008 | Packham | 137/614.04 |
| 7,357,792 | B2 | 4/2008 | Newton et al. | 604/244 |
| 7,396,348 | B2 | 7/2008 | Newton et al. | 604/256 |
| 7,497,848 | B2 | 3/2009 | Leinsing et al. | 604/247 |
| 7,497,849 | B2 | 3/2009 | Fangrow, Jr. | 604/247 |
| 7,510,545 | B2 | 3/2009 | Peppel | 604/256 |
| 7,815,168 | B2 | 10/2010 | Vangsness et al. | 251/149.2 |
| 8,100,869 | B2 | 1/2012 | Vangsness et al. | 604/249 |
| 2001/0004686 | A1 | 6/2001 | Huet | 604/240 |
| 2001/0042850 | A1 | 11/2001 | Cote, Sr. et al. | 251/149.1 |
| 2001/0049508 | A1 | 12/2001 | Fangrow, Jr. et al. | 604/256 |
| 2002/0029020 | A1 | 3/2002 | Cote, Sr. et al. | 604/247 |
| 2003/0050610 | A1 | 3/2003 | Newton et al. | 604/256 |
| 2003/0093061 | A1* | 5/2003 | Ganem | 604/533 |
| 2003/0098430 | A1 | 5/2003 | Leinsing et al. | 251/149.6 |
| 2003/0141477 | A1 | 7/2003 | Miller | 251/149.1 |
| 2004/0006330 | A1 | 1/2004 | Fangrow, Jr. | 604/533 |
| 2004/0049158 | A1 | 3/2004 | Ley et al. | 604/167.03 |
| 2004/0073171 | A1 | 4/2004 | Rogers et al. | 604/164.13 |
| 2004/0124388 | A1 | 7/2004 | Kiehne | 251/149.1 |
| 2004/0138626 | A1 | 7/2004 | Cote, Sr. et al. | 604/249 |
| 2004/0173769 | A1 | 9/2004 | deCler | 251/149.1 |
| 2005/0038397 | A1 | 2/2005 | Newton et al. | 604/249 |
| 2005/0087239 | A1 | 4/2005 | Kohda | 137/614.03 |
| 2005/0087241 | A1 | 4/2005 | Kohda | 137/614.03 |
| 2005/0090805 | A1 | 4/2005 | Shaw et al. | 604/523 |
| 2005/0121638 | A1 | 6/2005 | Doyle | 251/149 |
| 2005/0165365 | A1 | 7/2005 | Newton et al. | 604/246 |
| 2005/0222541 | A1 | 10/2005 | Lopez et al. | 604/249 |
| 2005/0228362 | A1 | 10/2005 | Vaillancourt | 604/533 |
| 2005/0256457 | A1 | 11/2005 | Rome | 604/167.06 |
| 2006/0108555 | A1 | 5/2006 | Kiehne | 251/149.7 |
| 2006/0129109 | A1 | 6/2006 | Shaw et al. | 604/246 |
| 2006/0142735 | A1 | 6/2006 | Whitley | 604/357 |
| 2006/0161115 | A1 | 7/2006 | Fangrow | 604/249 |
| 2006/0178645 | A1 | 8/2006 | Peppel | 604/249 |
| 2006/0200072 | A1 | 9/2006 | Peppel | 604/93.01 |
| 2006/0200088 | A1 | 9/2006 | Lopez et al. | 604/246 |
| 2006/0200089 | A1 | 9/2006 | Lopez et al. | 604/246 |
| 2006/0200090 | A1 | 9/2006 | Lopez et al. | 604/246 |
| 2006/0206061 | A1 | 9/2006 | Lopez et al. | 604/246 |
| 2006/0211997 | A1 | 9/2006 | Fangrow | 604/246 |
| 2006/0211998 | A1 | 9/2006 | Fangrow | 604/246 |
| 2006/0211999 | A1 | 9/2006 | Fangrow | 604/246 |
| 2006/0217671 | A1 | 9/2006 | Peppel | 604/246 |
| 2006/0264841 | A1 | 11/2006 | Cote, Sr. et al. | 604/247 |
| 2006/0264848 | A1 | 11/2006 | Fangrow | 604/249 |
| 2006/0264849 | A1 | 11/2006 | Lopez et al. | 604/249 |
| 2006/0270999 | A1 | 11/2006 | Fangrow | 604/249 |
| 2006/0271016 | A1 | 11/2006 | Fangrow | 604/539 |
| 2006/0293629 | A1 | 12/2006 | Cote, Sr. et al. | 604/246 |

(56) References Cited

U.S. PATENT DOCUMENTS

| | | | |
|---|---|---|---|
| 2007/0012893 A1 | 1/2007 | Lee et al. | 251/149.1 |
| 2007/0083162 A1 | 4/2007 | O'Reagan et al. | 604/167.03 |
| 2007/0100284 A1 | 5/2007 | Leinsing et al. | 604/164.01 |
| 2007/0112312 A1 | 5/2007 | Fangrow | 604/246 |
| 2007/0112313 A1 | 5/2007 | Fangrow | 604/246 |
| 2007/0218757 A1 | 9/2007 | Guala | 439/589 |
| 2007/0235674 A1 | 10/2007 | Vangsness et al. | 251/149.2 |
| 2007/0235675 A1 | 10/2007 | Kimball et al. | 251/149.2 |
| 2007/0235676 A1 | 10/2007 | Vangsness et al. | 251/149.2 |
| 2007/0238337 A1 | 10/2007 | Kimball et al. | 439/157 |
| 2007/0246674 A1 | 10/2007 | Kiehne | 251/149.6 |
| 2007/0255229 A1 | 11/2007 | Kane et al. | 604/248 |
| 2007/0260195 A1 | 11/2007 | Bartholomew et al. | 604/244 |
| 2007/0270756 A1 | 11/2007 | Peppel et al. | 604/167.06 |
| 2008/0027398 A1 | 1/2008 | McKinnon et al. | 604/264 |
| 2008/0027415 A1 | 1/2008 | Isaacson et al. | 604/539 |
| 2008/0039802 A1 | 2/2008 | Vangsness et al. | 604/247 |
| 2008/0172003 A1 | 7/2008 | Plishka et al. | 604/249 |
| 2008/0172005 A1 | 7/2008 | Jepson | 604/249 |
| 2008/0190485 A1 | 8/2008 | Guala | 137/1 |
| 2008/0275405 A1 | 11/2008 | Newton et al. | 604/256 |
| 2009/0057589 A1 | 3/2009 | Thorne, Jr. et al. | 251/149.1 |
| 2009/0105666 A1 | 4/2009 | Peppel | 604/249 |

FOREIGN PATENT DOCUMENTS

| | | | | |
|---|---|---|---|---|
| EP | 0 791 371 A1 | 8/1997 | | A61M 39/26 |
| EP | 1 243 285 A | 9/2002 | | A61M 39/02 |
| GB | 2 079 162 A | 1/1982 | | A62B 9/02 |
| JP | 2001-505102 A | 4/2001 | | A61M 5/168 |
| JP | 2001-212235 A | 8/2001 | | A61M 5/168 |
| JP | 2008-522736 A | 7/2008 | | A61M 39/02 |
| WO | WO 83/02559 A1 | 8/1983 | | A61M 5/00 |
| WO | WO 93/11828 A1 | 6/1993 | | A61M 39/00 |
| WO | WO 96/00107 A1 | 1/1996 | | A61M 39/26 |
| WO | WO 97/39791 A1 | 10/1997 | | A61M 39/00 |
| WO | WO 98/22178 A1 | 5/1998 | | A61M 39/26 |
| WO | WO 98/26835 A1 | 6/1998 | | A61M 39/26 |
| WO | WO 98/39594 A1 | 9/1998 | | F16L 37/28 |
| WO | WO 00/44433 A2 | 8/2000 | | A61M 39/00 |
| WO | WO 01/20218 A1 | 3/2001 | | F16L 29/00 |
| WO | WO 03/018104 A1 | 3/2003 | | A61M 39/00 |
| WO | WO 03/018105 A1 | 3/2003 | | A61M 39/24 |
| WO | WO 2004/006046 A2 | 1/2004 | | |
| WO | WO 2006/062912 A1 | 6/2006 | | A61M 39/04 |

OTHER PUBLICATIONS

Sylvie Reinbold, Authorized Officer European Patent Office, Notification Concerning Transmittal of International Preliminary Report on Patentability (Chapter I of the Patent Cooperation Treaty)—Application No. PCT/US2010/039333, dated Jan. 4, 2012 (8 pages).

Japanese Patent Office, Official Action—Application No. 2012-516368, dated May 16, 2014 (3 pages).

Japanese Patent Office, Official Action—Application No. 2012-516368, dated May 16, 2014 (6 pages), [English Translation].

US 6,971,630, 12/2005, Leinsing et al. (withdrawn)

* cited by examiner

MEDICAL VALVE WITH IMPROVED BACK-PRESSURE SEALING

PRIORITY

This application is a continuation of and claims priority from co-pending U.S. patent application Ser. No. 12/819,551, entitled "Medical Valve with Improved Back-Pressure Sealing," filed Jun. 21, 2010, and naming William Siopes, Luis Maseda and Ian Kimball as inventors, the disclosure of which is incorporated herein, in its entirety, by references.

U.S. patent Ser. No. 12/819,551, in turn, claims priority from U.S. Provisional Patent Application No. 61/219,319, filed Jun. 22, 2009, entitled, "Medical Valve with Improved Back-Pressure Sealing," and naming William Siopes, Luis Maseda and Ian Kimball as inventors, the disclosure of which is incorporated herein, in its entirety, by reference.

TECHNICAL FIELD

The invention generally relates to medical valves and, more particularly, the invention relates to improving resistance to proximally directed forces in medical valves.

BACKGROUND ART

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring the patient's skin be repeatedly pierced by a needle.

Medical personnel insert a medical instrument into the medical valve to inject fluid into (or withdraw fluid from) a patient who has an appropriately secured medical valve. Once inserted, fluid may be freely injected into or withdrawn from the patient.

SUMMARY OF THE INVENTION

In accordance with one embodiment of the present invention, a medical valve transitions between an open mode that permits fluid flow, and a closed mode that prevents fluid flow. The medical valve has a housing with an inlet, an outlet, and at least one relief zone that is in fluid communication with the outlet when the valve is in the closed mode. The medical valve may also have a plug member that is movably mounted within a passageway. The plug member has a proximal end, a distal end, and a hole between its proximal and distal ends. The valve may also have a gland member with a first seal member that seals the hole when the valve is in the closed mode. The relief zone may be radially outward of the seal member.

In some embodiments, the medical valve may also have a second seal member located proximal to the hole when the valve is in the closed mode. In such embodiments, the first seal member may be located distal to the hole when the valve is in the closed mode. The first and second seal members may be o-rings and may or may not be integral to the gland member. The housing of the medical valve may have a plurality of ribs, that define the relief zone(s). The housing may also have a shelf portion that, in conjunction with the ribs, supports a portion of the gland member. Additionally, the housing may have guide posts at the outlet of the valve that center the plug member within the outlet as the plug member moves distally. In some embodiments, the shelf portion and the guide posts may be part of the ribs.

In accordance with still further embodiments, the relief zone(s) may be configured such that a proximally directed pressure within the valve increases the seal at the hole by creating a radially inward pressure on the resilient member and the first and/or second seal member(s). As the valve transitions from the closed mode to the open mode, the gland member may deform into the relief zone.

In accordance with additional embodiments of the present invention, a resilient member for a medical valve having a housing with an inlet and an outlet may include a body portion and a first seal member. The body portion may be located within the housing, and at least a portion of the body portion may be supported by the housing. The housing may at least one relief zone in fluid communication with the outlet of the valve. The first seal member may create a first seal against a plug member that is moveably mounted within a passageway in the valve. The first seal member may seal a hole in the plug member when the valve is in the closed mode. The relief zone may be radially outward of the first seal member.

In other embodiments, the resilient member may have a second seal member that is located proximal to the hole when the valve is in the closed mode. In such embodiments, the first seal member may be located distal to the hole when the valve is in the closed mode. The first and second seal members may be o-rings and may or may not be integral to the resilient member.

The housing may include a shelf portion and a plurality of rib members, which define the relief zone(s), The shelf portion may support the resilient member within the housing and, during valve operation, the body portion of the resilient member may deform into the relief zones. The relief zone(s) may be configured such that, in the presence of a proximally directed pressure within the valve, fluid entering the relief zone applies a radially inward pressure on the resilient member and increases the seal at the hole.

In accordance with other embodiments of the present invention a housing for a medical valve includes a proximal portion with an inlet, and a distal portion with an outlet. The proximal portion and the distal portion may secure a resilient member within the interior of the housing. The resilient member or seal members located on the resilient member may seal a transverse hole location in a plug member. The housing may also have a relief zone in fluid communication with the outlet. In the presence of a proximally directed pressure through the medical valve, the relief zone may be configured to increase the seal provided by the resilient member and/or seal members. The relief zone may be radially outward of the hole.

A shelf portion located within the distal portion of the housing may support the resilient member. Additionally, the housing may also have a plurality of rib members located within the distal portion. The plurality of rib members may define the relief zone(s). The resilient member may include a first seal member located proximal to the hole and a second seal member located distal to the hole. The first seal member and the second seal member may seal the hole, and the proximally directed pressure through the valve may increase the seal created by the first and second seal members around the hole. The relief zone may be radially outward of the second seal member. The housing may also have guide posts at the outlet that center the plug member within the outlet as the plug member moves distally and/or proximally.

In accordance with additional embodiments of the present invention, a medical valve having an open mode that permits fluid flow, and a closed mode that prevents fluid flow may include a housing, a rigid member, and a resilient member. The housing may have an inlet, an outlet, and at least one relief zone in fluid communication with the outlet when the valve is in the closed mode. The rigid member may be moveably mounted within the passageway. The rigid member may also have a proximal end, a distal end, and a flow channel passing through it. The flow channel may have an opening nearer the distal end of the rigid member. The resilient member may have a proximal portion and sealing portion with a normally closed aperture. The sealing portion may be distal to the proximal portion, and the relief zone may be radially outward of the sealing portion. The sealing portion may seal the valve and prevent fluid from passing through the valve when in the closed mode.

The medical valve may also have plurality of ribs that define the relief zone(s). The relief zone(s) may be configured such that a proximally directed pressure within the valve increases the seal provided by the sealing portion by creating a radially inward pressure on the sealing portion and the aperture. During valve actuation, a portion of the resilient member may deform into the relief zone(s) as the valve transitions from the closed to open modes.

In accordance with other embodiments, the rigid member may be a cannula. The cannula may pass through the aperture within the sealing portion when the valve transitions from the closed mode to the open mode to create fluid communication between the valve inlet and valve outlet. Alternatively, the rigid member may be an actuator with a body portion and a plurality of leg members extending from the body portion. Distal movement of the actuator may cause the leg members to interact with the resilient member to open the aperture, which, in turn, transition the valve from the closed to the open mode.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, a medical valve has a relief zone that is in fluid communication with a valve outlet. The relief zone provides the valve with dynamic sealing in the presence of a proximally directed pressure. Details of illustrative embodiments are discussed below.

Figure 1:
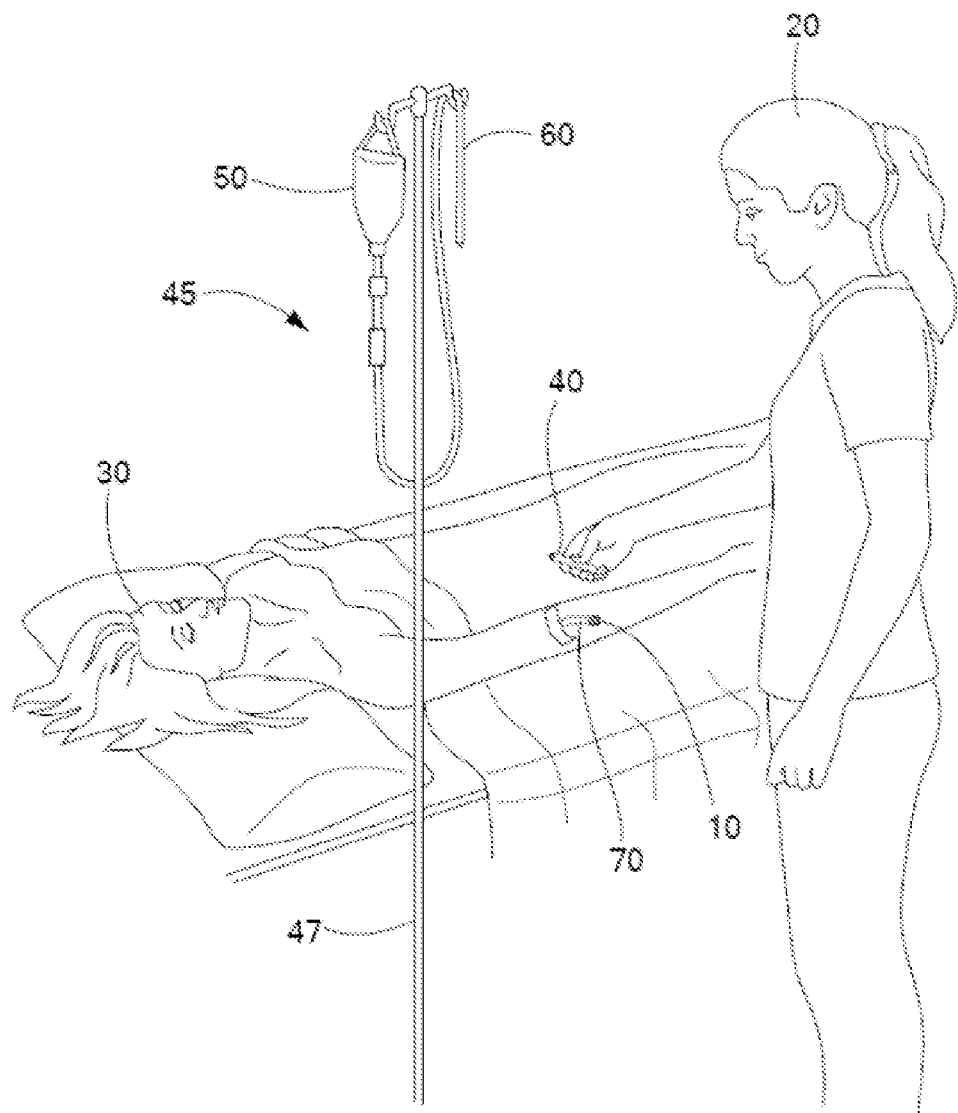
FIG. 1 schematically shows one use of a medical valve configured in accordance with one embodiment of the present invention.

FIG. 1 schematically shows one illustrative use of a medical valve 10 configured in accordance with illustrative embodiments of the invention. In this example, a catheter 70 connects the valve 10 with a patient's vein (the patient is identified by reference number 30). Adhesive tape or similar material may be coupled with the catheter 70 and patient's arm to ensure that the valve remains in place.

After the valve 10 is in place, a nurse, doctor, technician, practitioner, or other user (schematically identified by reference number 20) may intravenously deliver medication to the patient 30, who is lying in a hospital bed. To that end, after the valve is properly primed and flushed (e.g., with a saline flush), the nurse 20 swabs the top surface of the valve 10 to remove contaminants. Next, the nurse 20 uses a medical instrument (e.g., a syringe having a distally located blunt, luer tip complying with ANSI/ISO standards) to inject medication into the patient 30 through the valve 10. For example, the medical practitioner 20 may use the valve 10 to inject drugs such as heparin, antibiotic, pain medication, other intravenous medication, or other fluid deemed medically appropriate. Alternatively, the nurse 20 (or other user) may withdraw blood from the patient 30 through the valve 10.

The medical valve 10 may receive medication or other fluids from other means, such as through a gravity feed system 45. In general, traditional gravity feeding systems 45 often have a bag 50 (or bottle) containing a fluid (e.g., anesthesia medication) to be introduced into the patient 30. The bag 50 (or bottle) typically hangs from a pole 47 to allow for gravity feeding. The medical practitioner 20 then connects the bag/bottle 50 to the medical valve 10 using tubing 60 having an attached blunt tip. In illustrative embodiments, the blunt tip of the tubing has a luer taper that complies with the ANSI/ISO standard. After the tubing 60 is connected to the medical valve 10, gravity (or a pump) causes the fluid to begin flowing into the patient 30. In some embodiments, the feeding system 45 may include additional shut-off valves on the tubing 60 (e.g., stop-cock valves or clamps) to stop fluid flow without having to disconnect the tubing 60 from the valve 10. Accordingly, the valve 10 can be used in long-term "indwell" procedures.

After administering or withdrawing fluid from the patient 30, the nurse 20 should appropriately swab and flush the valve 10 and catheter 70 to remove contaminants and ensure proper operation. As known by those skilled in the art, there is a generally accepted valve swabbing and flushing protocol that should mitigate the likelihood of infection. Among other things, as summarized above, this protocol requires proper flushing and swabbing before and after the valve is used to deliver fluid to, or withdraw fluid from the patient.

Figure 2A:
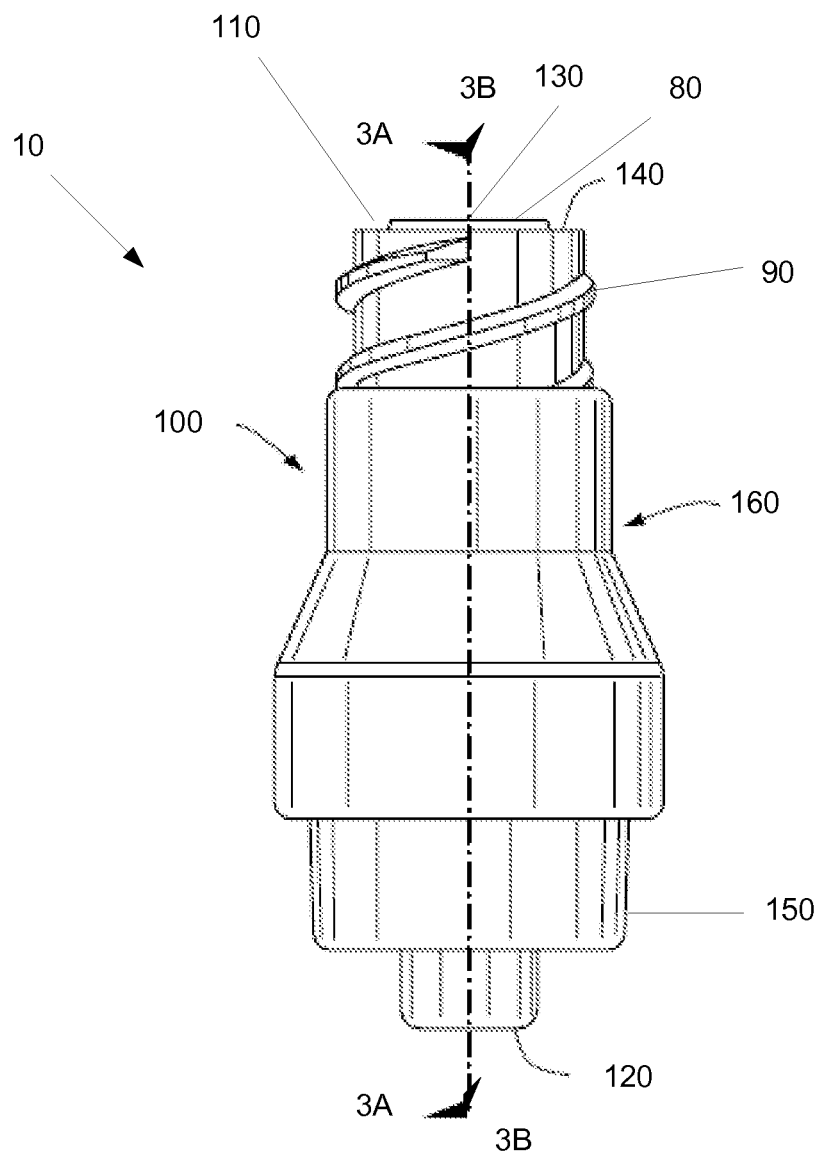
FIG. 2A schematically shows a perspective view of a medical valve configured in accordance with illustrative embodiments of the present invention.
Figure 2B:
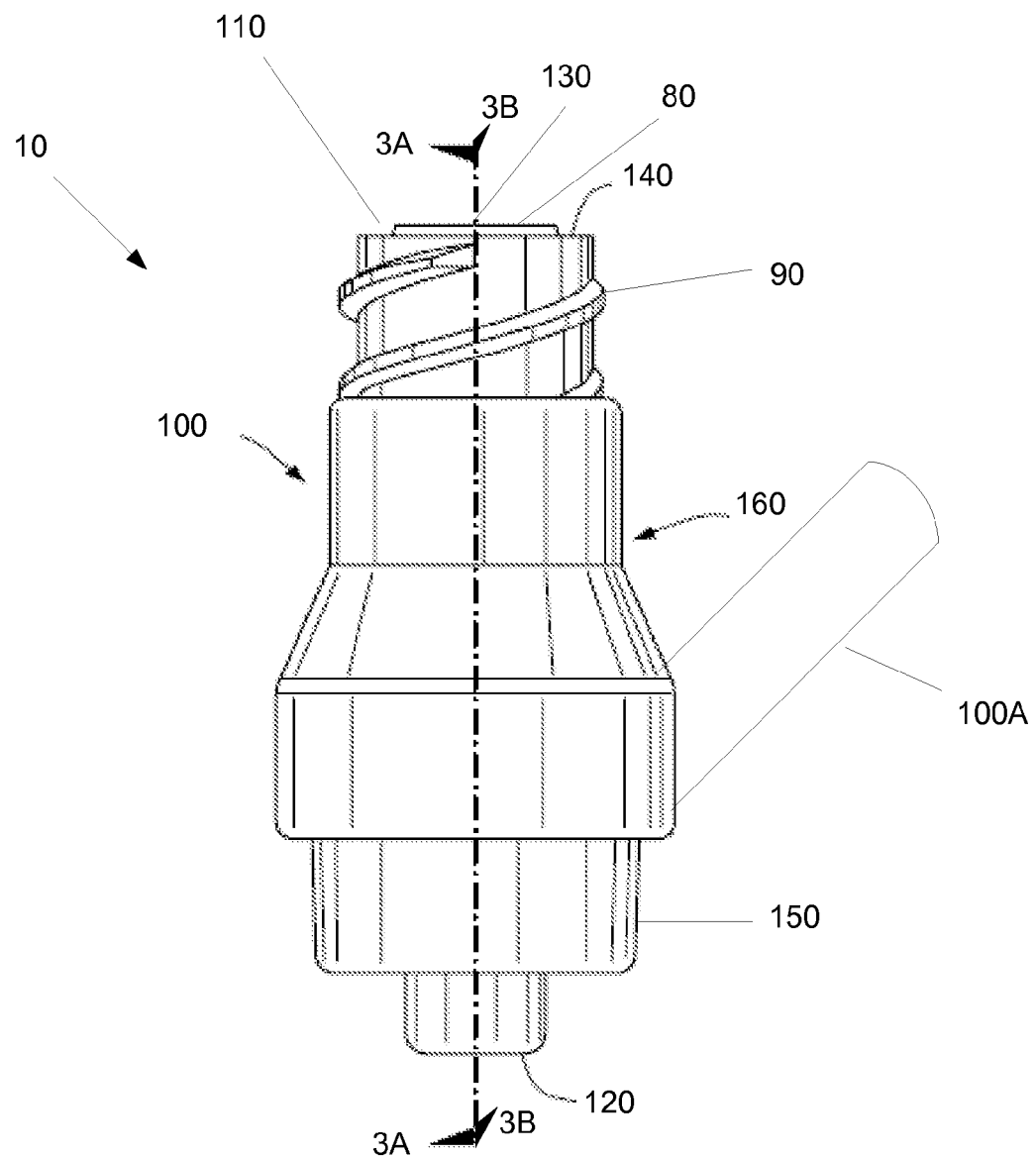
FIG. 2B schematically shows a perspective view of a medical valve of FIG. 2A with a Y-site branch.

As shown in FIGS. 2A and 2B, the valve 10 has a housing 100 forming an interior having a proximal port 110 for receiving the instrument 40, and a distal port 122. The valve 10 has an open mode that permits fluid flow through the valve 10, and a closed mode that prevents fluid flow through the valve 10. To that end, the interior contains a valve mechanism that selectively controls (i.e., allow/permits) fluid flow through the valve 10. The fluid passes through a complete fluid path that extends between the proximal port 110 and the distal port 122.

It should be noted that although much of the discussion herein refers to the proximal port 110 as an inlet, and the distal port 122 as an outlet, the proximal and distal ports 110 and 120 also may be respectively used as outlet and inlet ports. Discussion of these ports in either configuration therefore is for illustrative purposes only.

The valve 10 is considered to provide a low pressure seal at its proximal end 110. To that end, the proximal end 110 of the medical valve 10 has a resilient proximal gland 80 with a resealable aperture 130 that extends entirely through its profile. The aperture 130 may, for example, be a pierced hole or a slit. Alternatively, the proximal gland 80 may be molded with the aperture 130. In some embodiments, when the valve 10 is in the closed mode, the aperture 130 may be held closed by the inner surface of the housing 100. In that case, the inner diameter of the proximal port 110 is smaller than the outer diameter of the proximal gland 80 and thus, the proximal port 110 squeezes the aperture 130 closed. Alternatively, the resilient member may be formed so that the aperture 130 normally stays closed in the absence of a radially inward force provided by the inner diameter of the proximal port 110. In other words, the proximal gland 80 is formed so that the aperture 130 normally is closed.

The proximal gland 80 may be flush with or extend slightly above the exterior inlet face 140 of the inlet housing 160. The proximal gland 80 and the exterior inlet face 140 thus present a swabbable surface, i.e., it may be easily wiped clean with an alcohol swab, for example, or other swab. Alternatively, the proximal gland 80 can be molded over the proximal port 110 to provide the swabbable surface. Such valves typically have been referred to in the art as "swabbable valves." Various other embodiments, however, may relate to other types of valves and thus, not all embodiments are limited to swabbable valves. In addition, some embodiments may be used with instruments 40 having blunt tips that do not comply with the ANSI/ISO luer standard.

The outside surface of the valve proximal port 110 may also have inlet threads 90 for connecting the medical instrument 40. Alternatively or in addition, the proximal end may have a slip design for accepting instruments 40 that do not have a threaded interconnect. In a similar manner, the distal end of the valve 10 has a skirt 150 containing threads 280 (see FIGS. 3A and 3B) for connecting a threaded port of the catheter of FIG. 1, or a different medical instrument, to the valve distal port 122. The proximal end inlet threads 90 and the distal end threads 280 preferably comply with ANSI/ISO standards (e.g., they are able to receive/connect to medical instruments complying with ANSI/ISO standards). In addition to the threads described above, the internal geometry of the inlet housing 160 (e.g., shown in FIGS. 3A and 3B) may taper in an opposite direction to that of a standard luer taper.

It should be noted that the above embodiments describe a medical valve 10 in which the proximal port 110 and the distal port 122 are aligned with one another. However, in various other embodiments of the present invention, the medical valve 10 can include a Y-site branch 100A (e.g., see FIG. 2B). The Y-site branch 100A may extend from the housing 100 to form a Y-site channel. The Y-site channel may be in fluid communication with the valve distal port 122. To ensure sterility, the Y-site channel may have a resilient diaphragm, or a valve of some type. Alternatively, the Y-site channel may have no valving means.

Figure 3B:
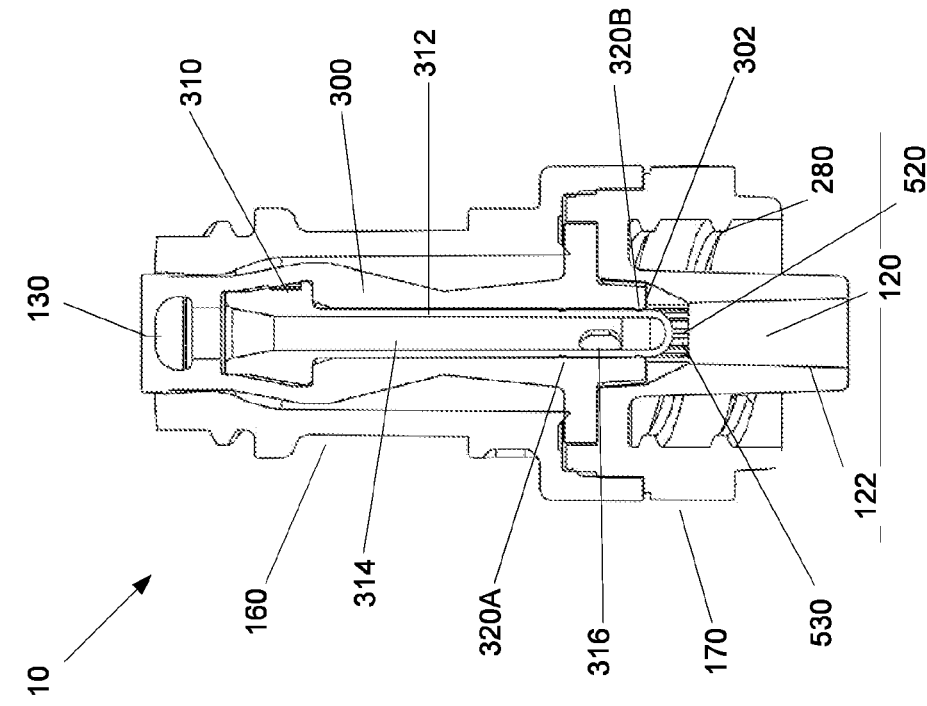
FIG. 3B schematically shows a cross-sectional view of the valve shown in FIG. 2A in the closed mode along line 3B-3B.
Figure 3A:
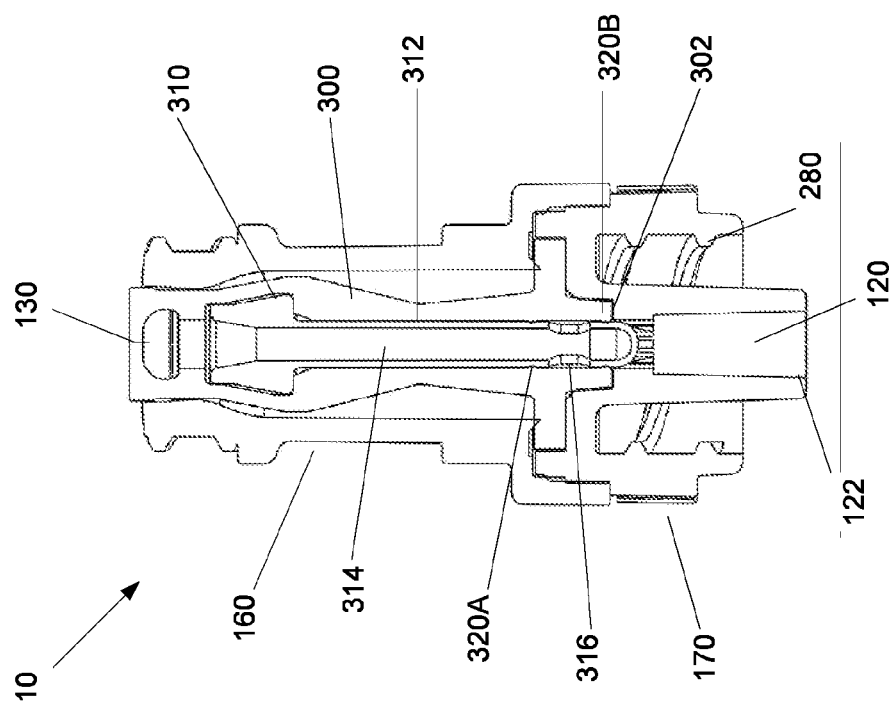
FIG. 3A schematically shows a cross-sectional view of the valve shown in FIG. 2A in the closed mode along line 3A-3A.

FIG. 3A schematically shows the cross section of the valve shown in FIG. 2A along the line 3A-3A. FIG. 3B schematically shows the cross section of the valve shown in FIG. 2A along the line 3B-3B. FIGS. 3A and 3B show the valve 10 in the closed position when no medical instrument or other instrument is inserted through the proximal port 110. As shown, the housing 100 includes an inlet housing 160 and an outlet housing 170, which connect together to form the interior of the medical valve 10. Within the interior, the medical valve 10 has a valve mechanism. The inlet housing 160 and the outlet housing 170 may be joined together in a variety of ways, including a snap-fit connection, ultrasonic welding, plastic welding, or other method conventionally used in the art.

The internal valve mechanism controls fluid flow through the valve 10. The valve mechanism includes a resilient member 300 (e.g., a stretchable and compressible gland/gland member) secured between the inlet housing 160 and outlet housing 170, and a rigid and longitudinally movable plug member 310 (e.g., a cannula) secured within the valve 10 by the resilient member 300, which, as described in greater detail below, prevents fluid flow through the plug member 310 when the valve is in the closed mode.

The plug member 310 includes a proximal section and a distally located thin section. In illustrative embodiments, the thin section is a hollow needle (identified by reference number "312") that, together with the proximal section, form a flow channel 314. Alternatively, the plug member 310 can have a larger inner diameter. The needle 312 is open at its proximal end, closed at its distal end, and has a hole 316 (e.g., a transverse hole) in its side just proximal to its distal end. When in the closed position, the hole 316 is sealed by seal members 320A and 320B. The interaction of the seal members 320A and 320B with the plug member 310 will be discussed in greater detail below.

It is important to note that, although the needle 312 is described above as having a single hole, other embodiments of the present invention may have multiple holes within the needle 312. For example, the needle 312 can have a transverse hole that essentially creates two holes spaced 180 degrees apart. Alternatively, the needle can have three or more holes spaced radially apart from one another along the diameter of the needle.

It is also important to note that, although the hole 316 is described above as being just proximal to the needle's distal end, other embodiments of the present invention may have the hole 316 located at other positions along the length of the needle 312. For example, the hole 316 may be located at a mid-point of the needle 312 or close to the proximal end of the needle 312. Therefore, depending on the location of the hole 316, the hole 316 may be located adjacent to and radially inward of the relief zones 530 (described in greater detail below) (e.g., if the hole 316 is just proximal to the needle's distal end) or proximal to and radially inward of the relief zones 530 (e.g., if the hole 316 is located at a mid-point or proximal end of the needle 312) when the valve 10 is in the closed mode.

Insertion of a nozzle against the slit 130 at the proximal end of the resilient member 300 (e.g., at proximal gland 80) causes the plug member 310 to move distally, thereby moving the hole 316 from its sealed position. Liquid consequently may be directed first through the flow channel 314 and hole 316, then out of the valve 10 through the outlet 120 distal port 122.

The outlet 120 has a volume that changes slightly as the needle 312 is urged proximally and distally by the nozzle. In particular, the volume of the outlet 120 is slightly greater when in the closed mode than when in the open mode. This slight difference in volume is due to the volume of the needle 312 extending into the outlet 120.

In an illustrative embodiment of the invention, the needle 312 is sized to be very thin. The amount of fluid drawn back into the outlet 120 as the nozzle is withdrawn corresponds to the volume of the needle 312 required to expose the hole 316 to the outlet 120. Consequently, as suggested above, this volume is controlled by the needle diameter and the placement of the hole 316. By making the diameter of the needle 312 small and the hole 316 very close to the distal end of the needle 312, the volume of fluid drawn back through the outlet 120 is reduced and the subsequent risk from contamination to the valve 10 minimized. In certain embodiments, the volume of fluid drawn back upon withdrawal of the nozzle is of the order of between about one and several microliters. In some embodiments, the total volume of fluid drawn back is on the order of about 0.5 microliters.

An exemplary embodiment of the invention may have a total length of about 1.160 inches, a maximum width of about 0.440 inches, and a priming volume of 0.030-0.050 cubic centimeters. The priming volume is measured as the volume required to fill the valve completely when in the open state.

Conversely, other embodiments of the invention may have either a neutral displacement or a positive displacement upon insertion and/or withdrawal of the nozzle. For example, embodiments exhibiting neutral displacements will have substantially the same volume within the outlet 120 during the open mode and the closed mode. Embodiments exhibiting positive push upon withdrawal of the nozzle will have a smaller volume within the outlet 120 when the valve is in the closed mode as compared to the open mode.

As shown in FIGS. 3B, 5A, 5B, and 6, some embodiments of the present invention can have a variety of features that improve valve sealing and resistance to back-pressure and/or proximally directed pressures through the valve 10. For example, as mentioned above, the resilient member 300 may have a top plug member seal 320A located above (e.g., proximal to) the hole 316 within the plug member 310 and a bottom plug member seal 320B located below (e.g. distal to) the hole 316. Each seal provides additional sealing for the valve 10. In particular, the top plug member seal 320A prevents fluid within the valve 10 (e.g., at the outlet 120) from migrating up into the plug member/resilient member interface (e.g., the top plug member seal 320A prevents fluid from migrating up between the plug member 310 and the resilient member 300). The bottom plug member seal 320B seals the primary fluid path (e.g., the path through channel 314) and the hole 316 and prevents fluid from entering the plug member 310 from the outlet 120 of the valve 10 when the valve 10 is in the closed mode. Additionally, the bottom plug member seal 320B prevents fluid from passing through the valve 10 and out the outlet 120 when the valve 10 is in the closed mode.

Although a variety of seal types and shapes may be used for the top plug member seal 320A and the bottom plug member seal 320B, embodiments of the present invention may utilize o-ring type seals that are integrated into the resilient member 300. To that end, the top plug member seal 320A and the bottom cannula plug member seal 320B may be formed into the resilient member 300 during manufacturing. The top plug member seal 320A and bottom plug member seal 320B may be made from the same material as the resilient member 300 or may be made from a separate material with different material characteristics (e.g., using a two-shot or overmold manufacturing process).

Figure 5B:
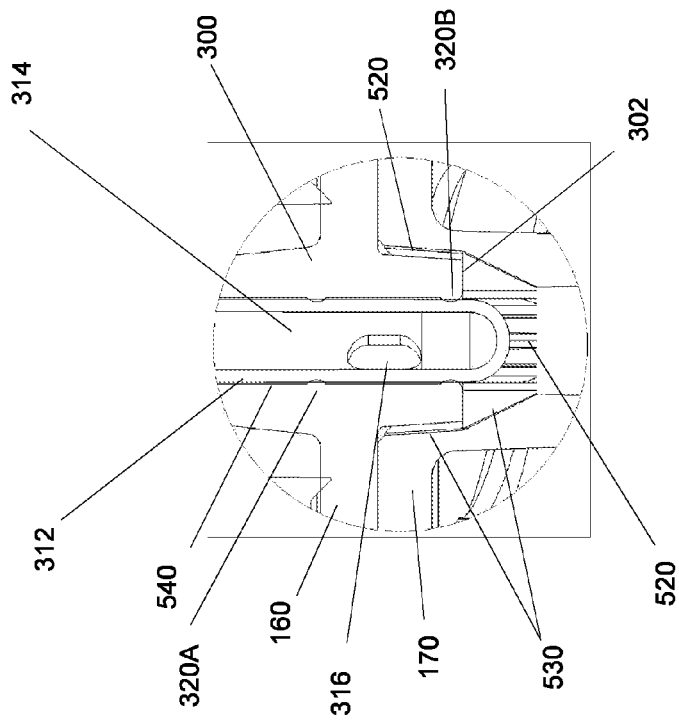
FIG. 5B schematically shows a detail view of the area 2 shown in FIG. 3B, in accordance with embodiments of the present invention.
Figure 5A:
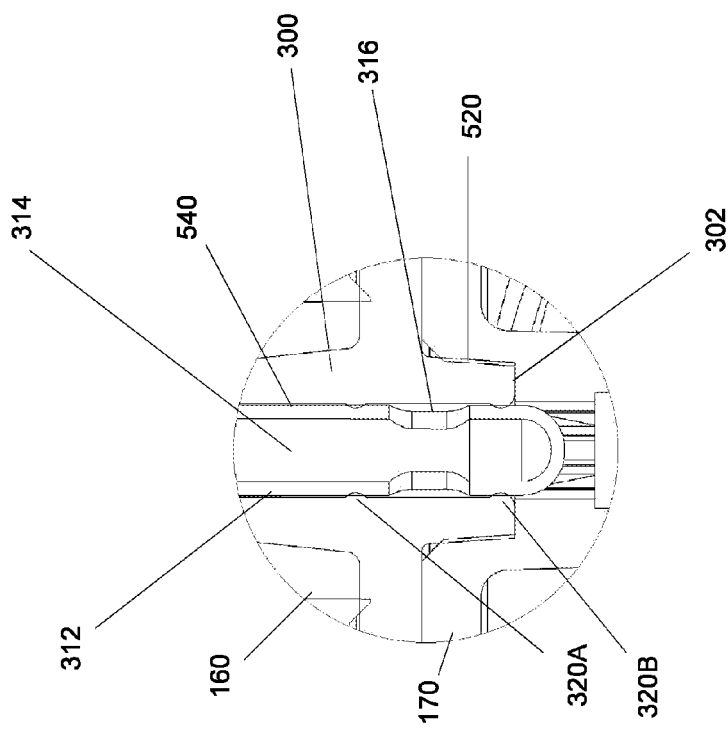
FIG. 5A schematically shows a detail view of the area 1 shown in FIG. 3A, in accordance with embodiments of the present invention.
Figure 6:
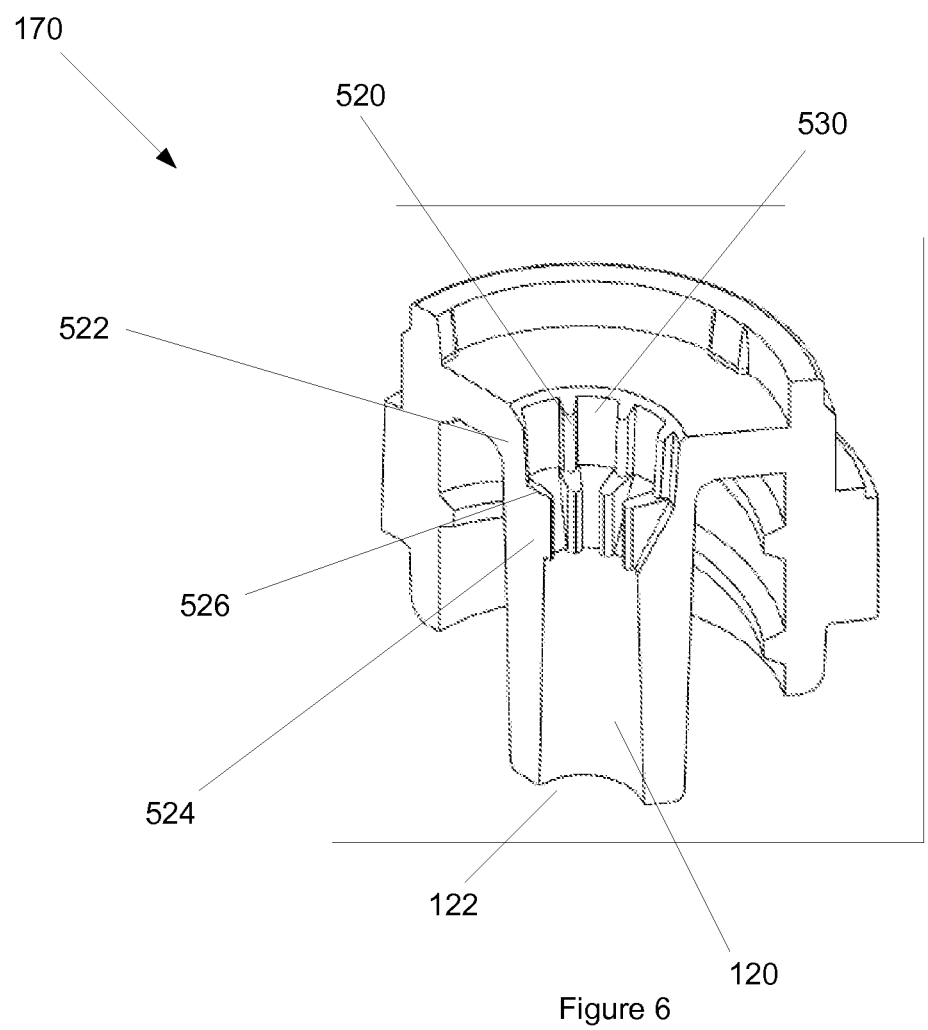
FIG. 6 schematically shows a pie-cut sectional view of the valve outlet, in accordance with embodiments of the present invention.

As best shown in FIGS. 5A, 5B, and 6, the outlet housing 170 may also have ribs 520 located near the outlet 120 of the valve 10. The ribs 520 may be spaced around the diameter of the outlet 120 such that they create relief zones 530 between each of the ribs 520 that are in fluid communication with the outlet 120. The functionality of the relief zones are discussed in greater detail below.

Each of the ribs 520 may be shaped such that they have a proximal portion 522, distal portion 524, and a shelf portion 526. Alternatively, the distal portions 524 and the shelf portions 526 may be part of the outlet housing 170 and separate from the ribs 520. In use, the proximal portion 522, and the shelf portion 526 may interact with the resilient member 300 to help seal the valve. For example, as best shown in FIGS. 5A and 5B, the shelf portion 526 may act as a rigid support for the distal end 302 of the resilient member 300. By supporting the resilient member 300 in this manner, the shelf portion 526 promotes deformation of the bottom plug member seal 320B (e.g., it causes the seal 320B to deform and expand inwardly toward the plug member 310) therefore, sealing of the hole 316. Additionally, the ribs 520 may be sized such that they preload the gland member and seals 320A and 320B by compressing the resilient member 300 (and the seals 320A and 320B) against the plug member 310. For example, embodiments of the ribs 520 may be sized to create a one thousandths or a two thousandths interference between the ribs 520 and the resilient member 300. By preloading the resilient member 300 and seals 320A and 320B, the proximal portions 522 of the ribs 520 help provide the seal around the hole 316.

It should be noted that the friction created by the seals 320A and 320B against the plug member 310 may resist the movement of the plug member 310 as the valve 10 transitions from the open mode to the closed mode and from the closed mode to the open mode (e.g., the friction created between the moving plug member 310 and the seals 320A and 320B may make movement of the plug member 310 difficult). To facilitate and aid the movement of the plug member 310 (e.g., as the valve opens or closes), the resilient member 300 may have a small annular volume 540 (e.g., a clearance) surrounding the plug member 310 in non-sealing areas. This annular volume 540 reduces the overall friction between the plug member 310 and the resilient member 300 by limiting the contact area to the seals 320A and 320B and allows the plug member 310 to move distally and proximally more easily. As mentioned above, the top plug member seal 320A prevents fluid from entering this annular volume 540.

As mentioned above and as shown in FIG. 6, some embodiments of the present invention may have relief zones 530 located between the ribs 520. In illustrative embodiments, the relief zones 530 enhance the sealing of the hole and are in fluid communication with the outlet 120 of the valve 10 when the valve 10 is in the closed mode. To that end, the relief zones 530 may provide dynamic fluid pressure sealing that enhances the seal around the hole 316 in the presence of a proximally directed pressure (e.g., a back-pressure). For example, because the relief zones 530 are in fluid communication with the outlet, the fluid generating the proximally directed pressure (e.g., air, blood, saline, etc.) may enter the relief zone, at which point, the fluid and the proximally directed pressure will create a radially inward pressure towards the resilient member 300. This radial inward pressure (e.g., axial pressure) will, in turn, further compress the seals 320A and 320B against the plug member 310 and increase the seal between the plug member 310 and the seal members 320A and 320B. In this manner, various embodiments of the valve 10 may have improved back-pressure resistance because, as the proximally directed pressure increases, the seal around the hole 316 will also increase, improving the valve's resistance to leakage in the presence of a back-pressure when in the closed mode.

In addition to providing a dynamic sealing mechanism while the valve 10 is in the closed mode, some embodiments of the relief zones 530 may also aid the valve 10 as it transitions from the closed mode to the open mode. For example, as the valve 10 transitions and the resilient member 300 begins to compress and deform (see FIG. 4), portions of the resilient member 300 may deform into the relief zones 530. By deforming into the relief zones 530, the resilient member 300 will be less likely to deform inwardly towards the plug member 310, which would increase the friction between the resilient member 300 and the plug member 310 and make it more difficult to transition between the closed and open modes. Additionally, the relief zones 530 help prevent the gland member from deforming distally and into the outlet 120 of the valve 10.

As mentioned above, the ribs 520 may have a distal portion 524. The distal portion 524 may be located below (e.g., distal to) the step portion 526 and may act as a guide, guide post, or a bearing for the plug member 310 as the valve 10 transitions between the open and closed modes. In particular, as the valve 10 begins to open, distal portion 524 of the ribs 520 will keep the plug member 310 generally centered within the outlet 120 as it moves distally within the valve 10. Likewise, upon valve closing, the distal portion 524 of the ribs 520 keeps the plug member 310 generally centered as it moves proximally within the valve 10. In this manner, the distal portion 524 of ribs 520 helps aid smooth operation of the valve 10 and may prevent the plug member 310 from becoming off-center within the valve and hindering the valve from either opening or closing. Additionally, the distal portion 524 of the ribs 520 may prevent the plug member 310 from hindering and/or disrupting fluid flow through the valve.

Figure 7A:
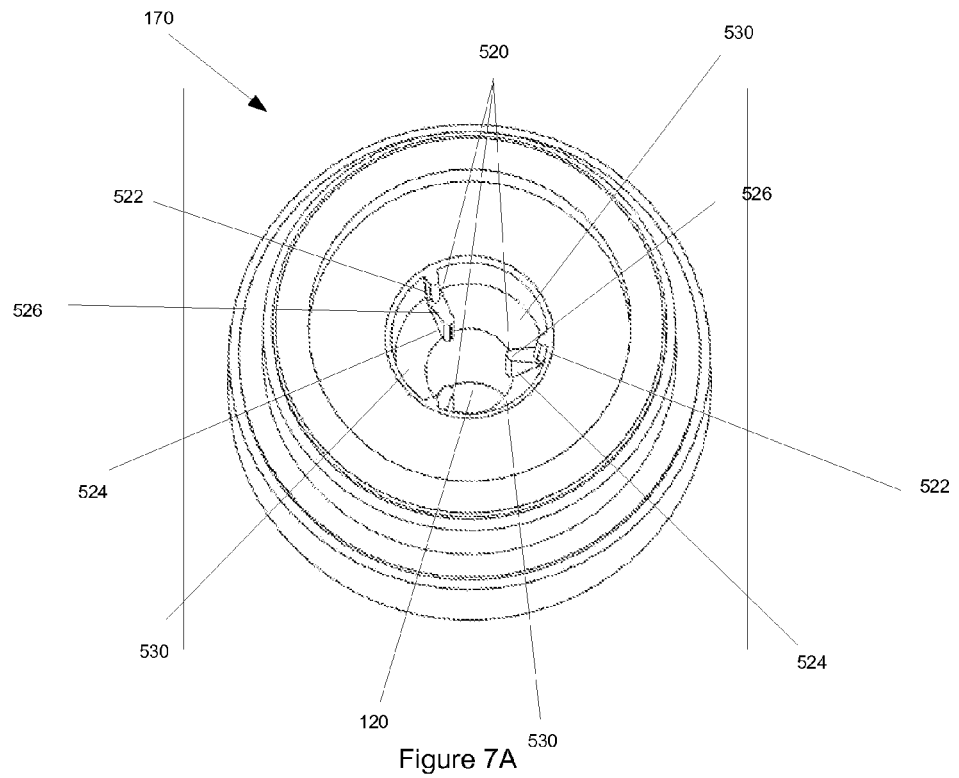
FIGS. 7A and 7B schematically show alternative embodiments of the valve outlet with differing numbers of ribs, in accordance with embodiments of the present invention.
Figure 7B:
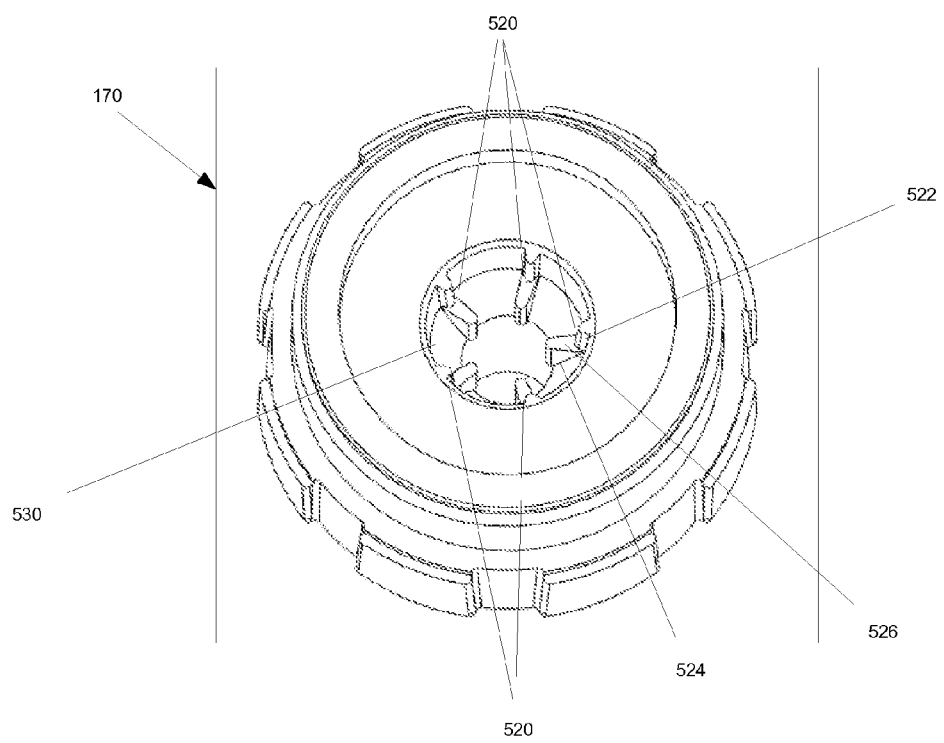

It is important to note that other embodiments of the present invention may have more or less ribs than that shown in FIG. 6 (or any of the other Figures). For example, as shown in FIG. 7A, some embodiments of the present invention may only have three ribs 520 equally spaced about the outlet housing 170. Alternatively, as shown in FIG. 7B, some embodiments may have 5 equally spaced ribs 520. However, these are provided as examples only. Other embodiments of the present invention may have more or less ribs 520 (e.g. an odd or even amount) and the ribs 520 may or may not be evenly spaced about the outlet housing 170.

Figure 4:
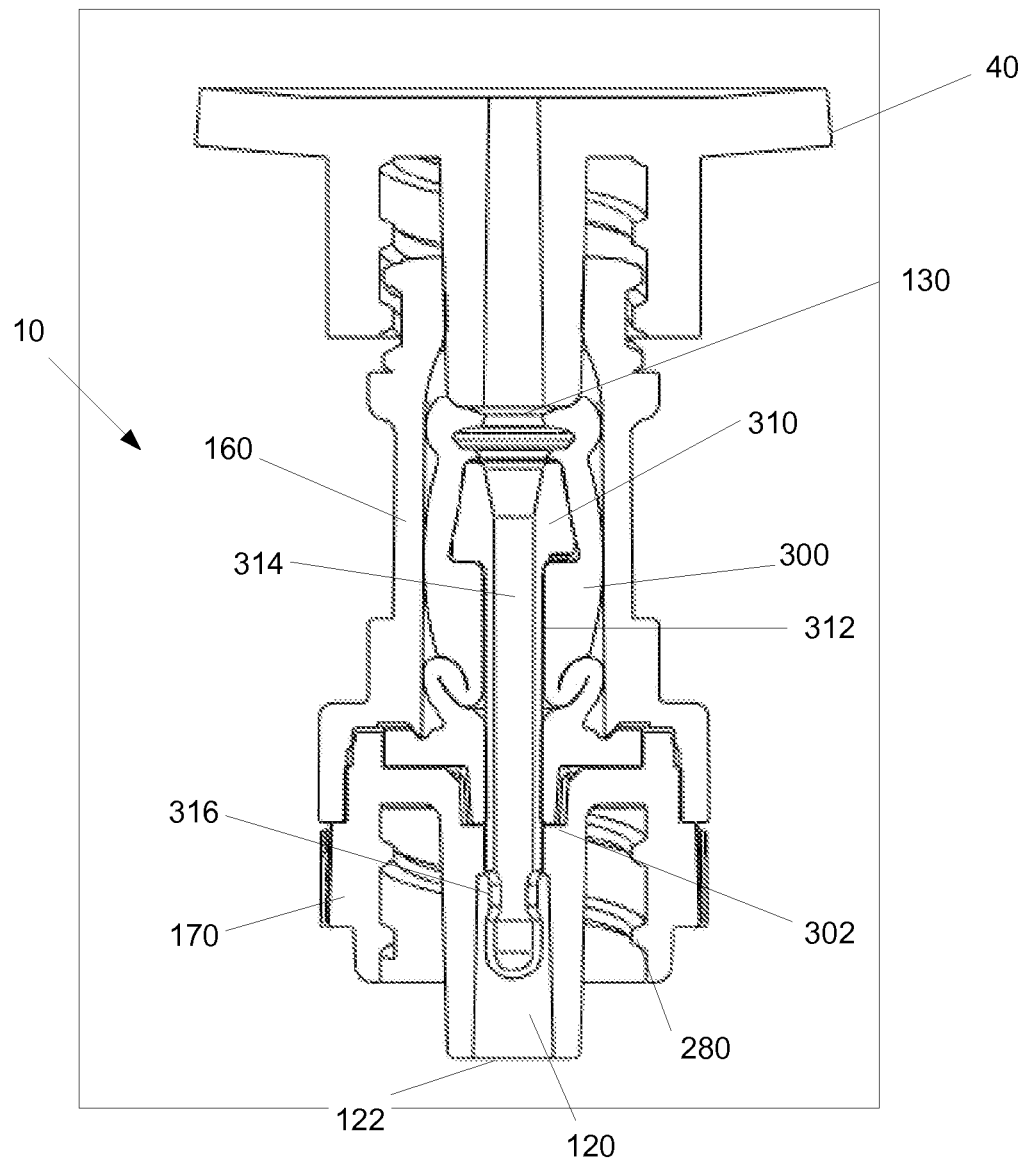
FIG. 4 schematically shows a cross-sectional view of the valve shown in FIG. 2A in the open mode along line 3A-3A.
Figure 8:
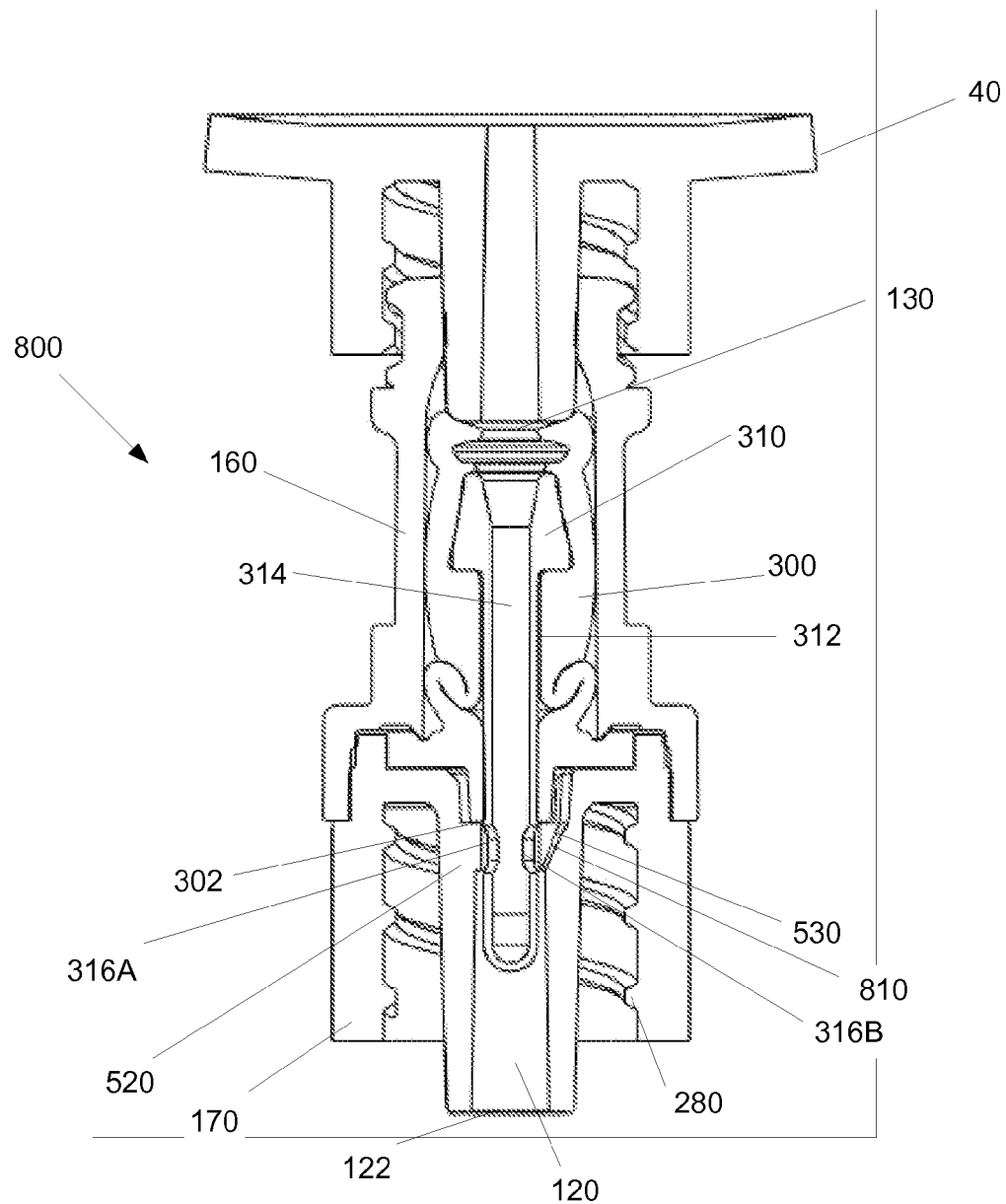
FIG. 8 schematically shows an alternative embodiment of a medical valve in the open mode, in accordance with embodiments of the present invention.

Although FIG. 4 shows the hole(s) 316 located below the ribs 5 when the valve is in the open mode, alternative embodiments of the present invention may have different hole 316 locations. For example, as shown in FIG. 8, alternative embodiments may have the hole(s) 316 located such that, when the valve 800 is in the open mode, the hole(s) 316 may be located within the rib/relief zone area 810. In such embodiments, when the fluid is transferred to the patient/subject (e.g., through the valve), the fluid will flow through the flow channel 314, out the hole(s) 316, into the relief zones 530, and out of the outlet 120. Alternatively, when fluid is drawn from the subject/patient, the fluid may enter the valve 800 through the outlet 120, flow into the relief zones 530 and the hole(s) 316, and through the flow channel 314.

In embodiments like that shown in FIG. 8, the orientation of the hole(s) 316 with respect to the ribs 520 may impact the flow through the valve 800. For example, if the plug member 310 has two holes (or a single transverse hole through the plug member 310 such that there is an opening on either side of the plug member 310) and the holes 316 are aligned with ribs 520, flow through the valve may be at least partially restricted (e.g., the ribs 520 may block a portion or all of the holes 316 and prevent or reduce flow through the holes 316). Accordingly, some embodiments may be configured to prevent restriction/alignment of at least one of the holes 316. For example, the plug member 310 may be oriented in such a way that the holes 316 do not align with the ribs 520.

Additionally or alternatively, the number of ribs 520 and the number of holes 316 may be set to prevent alignment of at least one hole 316 with a rib 520. For example, if the valve 10 has an odd number of evenly spaced ribs 520 (e.g., as shown in FIGS. 7A and 7B) and the plug member 310 has an even number of evenly spaced holes (e.g. two holes or the single transverse hole described above), even if one of the holes (e.g., hole 316A in FIG. 8) is aligned with a rib 520, the other hole (e.g., hole 316B in FIG. 8) will not be aligned with a rib 520 and, therefore, will be open to a relief zone 530. Flow through the hole 316B will be unrestricted.

Figure 9B:
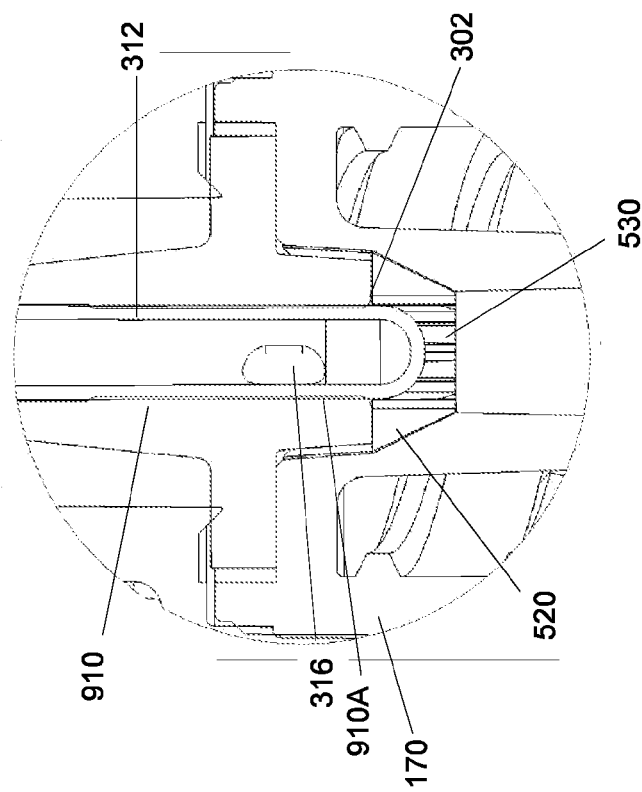
FIG. 9B schematically shows a detail view of the solid ring seal area of the medical valve shown in FIG. 9A, in accordance with embodiments of the present invention.
Figure 9A:
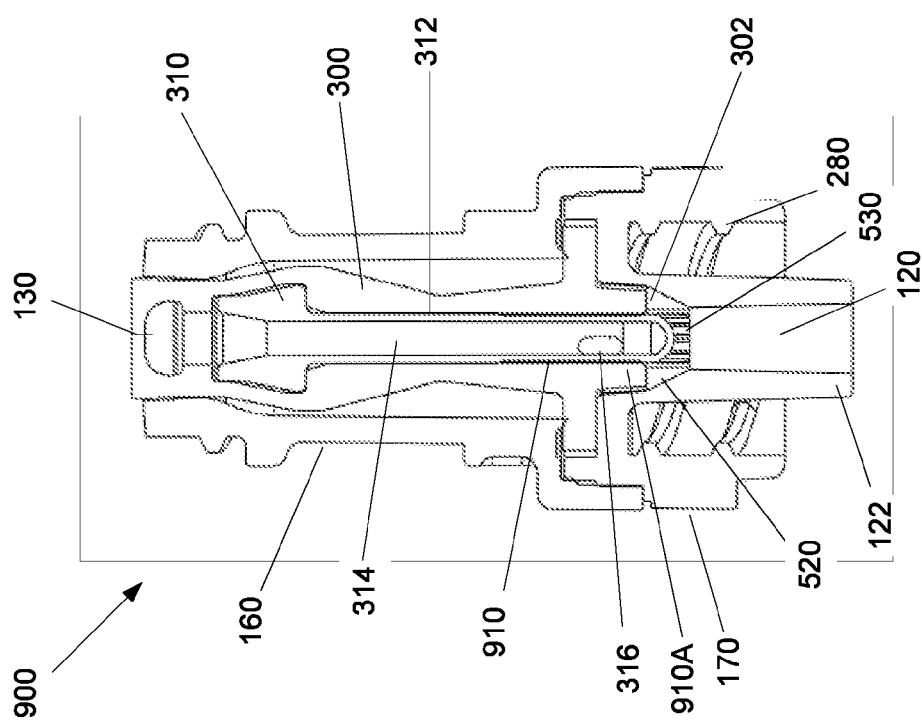
FIG. 9A schematically shows an additional alternative embodiment of a medical valve having a solid ring seal, in accordance with additional embodiments of the present invention.

It is also important to note that, although the above described embodiments refer to a resilient member 300 having seal members 320A and 320B, other embodiments may have different seal member structures and configurations. For example, as shown in FIGS. 9A and 9B, some embodiments may have a single, solid ring seal 910 that extends along a portion of the resilient member 300. The solid ring seal 910 may extend from below the hole 316 to a distance above the hole 316 and may provide a constant seal (e.g., against the plug member 310) along the length of the ring seal 910. Additionally, in some embodiments, the ring seal 910 may occlude the hole(s) 316 in the plug member 310 when the valve 900 is in the closed mode.

In embodiments having the ring seal 910, the ribs 520 and relief zones 530 will provide benefits similar to those described above for embodiments having seal members 320A and 320B. For example, the relief zones 530 may provide dynamic fluid pressure sealing that enhances the seal at the hole(s) 316 in the presence of a proximally directed pressure (e.g., a back-pressure). As discussed above, because the relief zones 530 are in fluid communication with the outlet, the fluid generating the proximally directed pressure (e.g., air, blood, saline, etc.) may enter the relief zones 530, at which point, the fluid and the proximally directed pressure will create a radially inward pressure towards the resilient member 300. This radial inward pressure (e.g., axial pressure) will, in turn, further compress at least a portion (e.g., portion 910A) of the solid ring seal 910 against the plug member 310 and increase the seal between the plug member 310 and the ring seal 910.

Figure 10A:
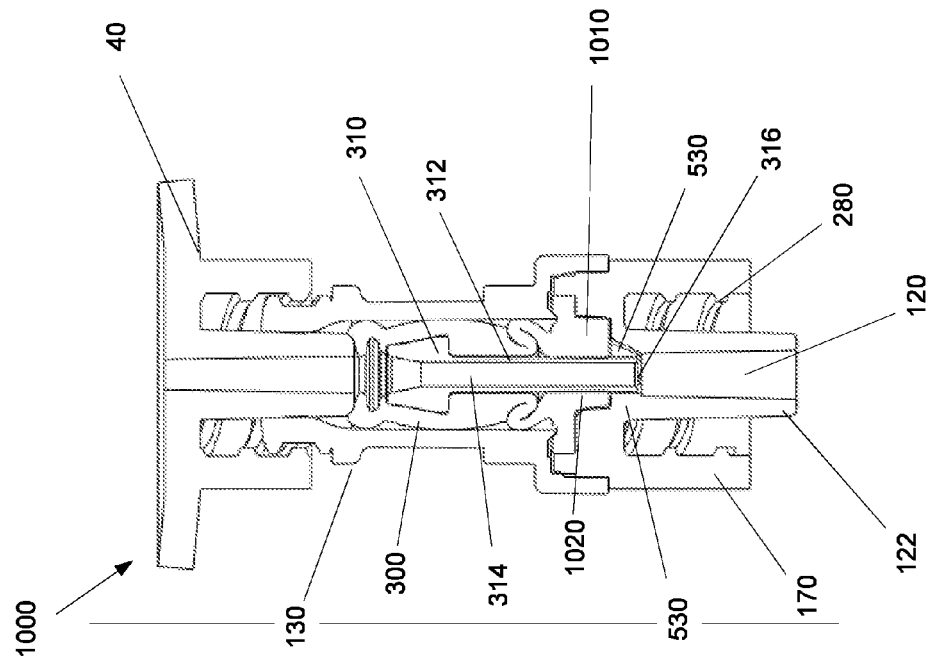
FIG. 10A schematically shows a cross-sectional view of an alternative embodiment of a medical valve in the closed mode, in accordance with embodiments of the present invention.
Figure 10B:
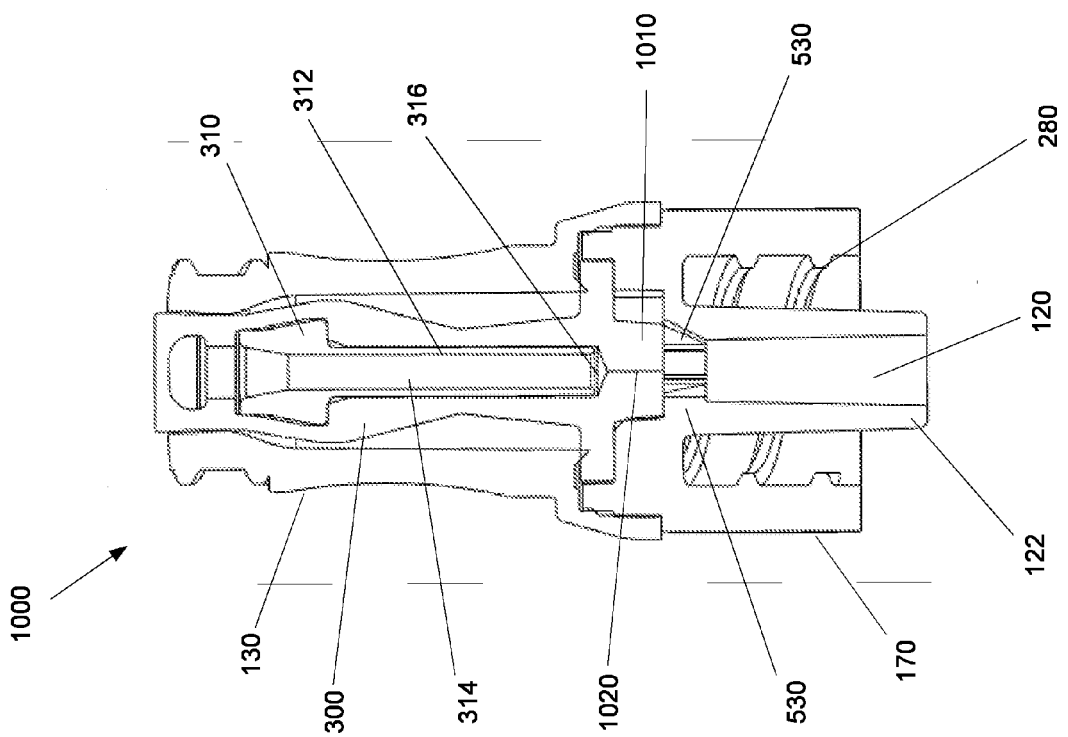
FIG. 10B schematically shows a cross-sectional view of the medical valve shown in FIG. 10A in the open mode, in accordance with embodiments of the present invention.

FIGS. 10A and 10B show an alternative embodiment of the medical valve 1000 in which the seal(s) providing the dynamic sealing are not radially outward from the plug member 310 (e.g., the plug member 310 does not extend into the sealing area), as shown in FIGS. 3A and 3B and as discussed above. In the embodiment shown in FIG. 10A, the hole(s) 316 within the plug member 310 may be located at the end of the plug member 310 and the seal member 1010 may be located distal to the plug member 310 and the hole(s) 316. The seal member 1010 may have a normally closed aperture 1020 (e.g., a slit) through which the plug member 310 may pass when the valve 1000 is transitioning from the open mode to the closed mode (see FIG. 10B).

In the presence of a proximally directed pressure (e.g., a back-pressure), the seal member 1010, in conjunction with ribs 520 and relief zones 530, will provide benefits similar to those described above for the other embodiments. For example, as discussed above, because the relief zones 530 are in fluid communication with the outlet, the fluid generating the proximally directed pressure (e.g., air, blood, saline, etc.) may enter the relief zones 530 and create a radially inward pressure towards the resilient member 300 and seal member 1010. This axial pressure will, in turn, apply a greater closing force on the normally closed aperture 1020 and increase the seal created by the aperture 1020 and the seal member 1010. It is important to note that, unlike some of the embodiments described above, embodiments with seal members 1010 do not seal against the plug member 310 when the valve is in the closed mode. The seal is created by keeping the aperture 1020 closed.

In operation, the medical valve 1000 shown in FIGS. 10A and 10B operates similar to those embodiments described above. For example, when a medical instrument 40 is inserted into the valve 1000, the resilient member 300 deforms and the plug member 310 moves distally to expose the hole(s) 316. However, as shown in FIG. 10B, the plug member 310 will open and pass through the aperture 1020 as it moves distally. This, in turn, will expose the hole(s) 316 to the outlet 120 and allow fluid to be transferred in or out of the patient/subject.

Figure 11:
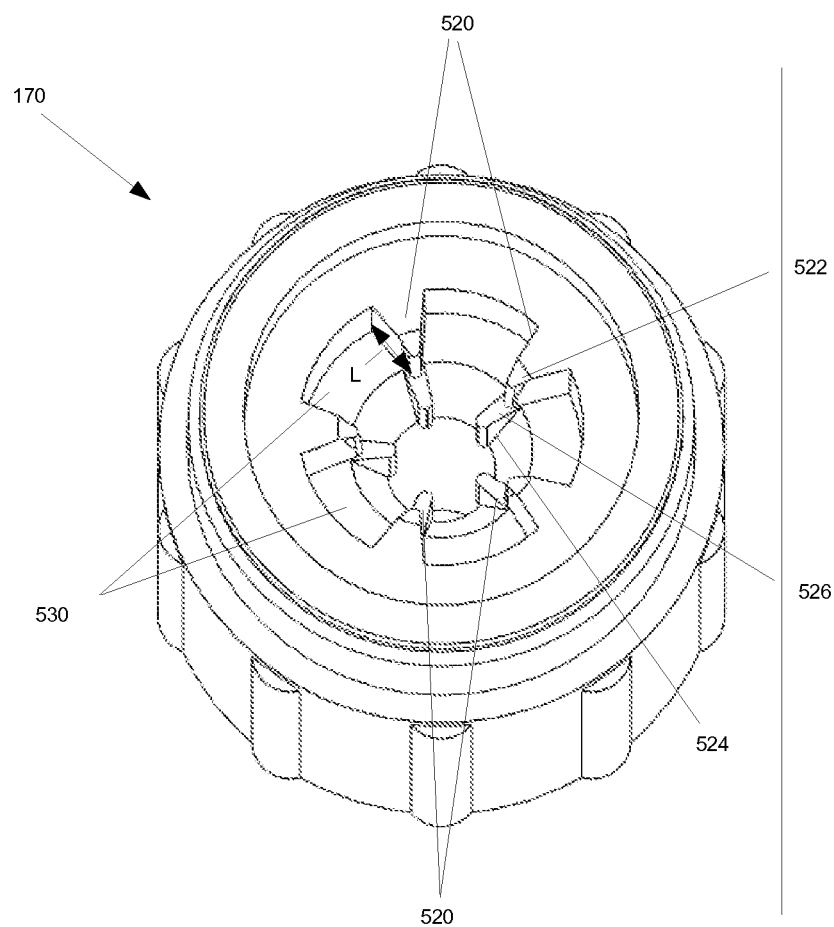
FIG. 11 schematically shows a valve outlet of the medical valve shown in FIGS. 10A and 10B, in accordance with embodiments of the present invention.

As shown in FIGS. 10A and 10B, the seal member 1010 may have a larger quantity of material than the seal members 320A/B described above. Accordingly, additional space may be required to allow the seal member 1010 to open and deform as the valve 1000 opens. To that end, the relief zones 530 contained within the outlet housing 170 may be enlarged. For example, as shown in FIG. 11, the relief zones 530 may be deeper than those shown in FIGS. 7A and 7B, to provide a greater space for the seal member 1010 to deform into. It is important to note that, although these deeper relief zones 530, in turn, increase the length L of the ribs 520, their functioning remains substantially unchanged.

Figure 12:
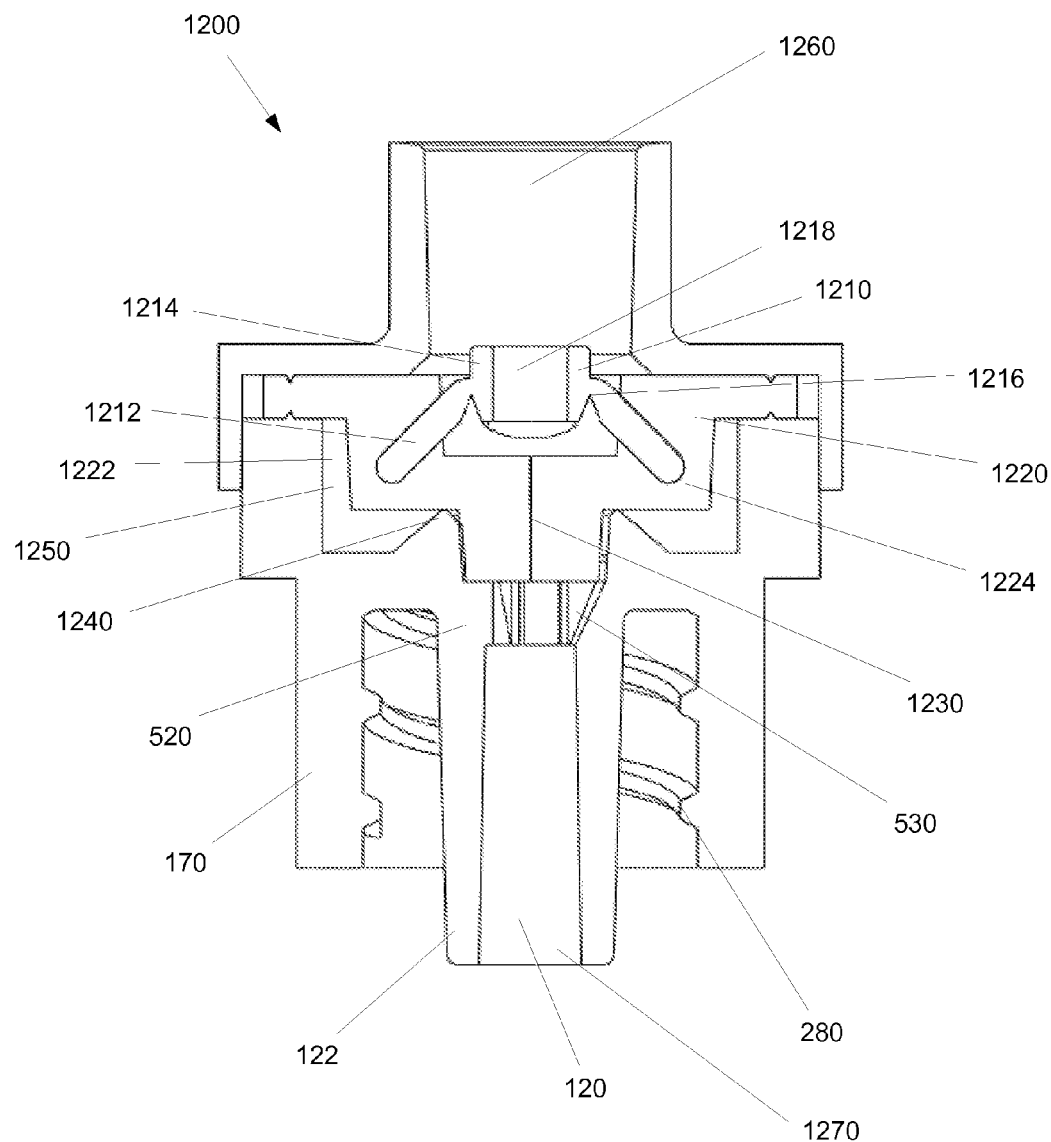
FIG. 12 schematically shows a cross-sectional view of an additional embodiment of a medical valve in accordance with embodiments of the present invention.

Although the above described embodiments utilize plug members 310 with holes 316 in conjunction with the gland member, other embodiments may utilize different internal valve mechanisms. For example, as shown in FIG. 12 some embodiments may utilize an actuator 1210 and gland member 1220. The actuator 1210 may have leg members 1212 extending out from a body portion 1214. As discussed in greater detail below, the leg members 1212 apply a force to the gland member 1220 as the actuator 1210 moves distally (e.g., when a medical implement is inserted into the valve 1200). The force applied to the gland member 1220 causes the gland member 1220 to deform causing an aperture 1230 through the gland member 1220 to open. Once the aperture 1230 is open, the valve 1200 is considered to be in the open mode.

To aid in the transition from the open mode and the closed mode, the valve 1200 can also include a valve seat 1240. The gland member 1220 can seal against the valve seat 1240 to prevent leakage past the valve seat 1240 and gland member 1220 and into space 1250. In some embodiments, the valve seat 1240 can be angled (as shown in FIG. 12). The angled valve seat 1240 aids in valve 1200 and aperture 1230 opening because the gland member 1220 can deform to the shape of the valve seat 1240 as the actuator 1210 moves distally.

As mentioned above, distal movement of the actuator 1210 opens the valve 1200. In particular, when a medical practitioner inserts a medical instrument into the valve 1200 and the actuator 1210 begins to move distally, the proximal portion 1222 of the gland member 1220 will begin to deform into space 1250. Specifically, in this embodiment, the actuator 1210 radially expands the gland member 1220 to open the valve 1200. As the gland member 1220 deforms, the aperture 1230 through the gland member 1220 opens, fluidly communicating the proximal port 1260 and the distal port 1270. The nurse or medical practitioner 20 can then transfer fluid to or from the patient 30.

As noted above, the actuator 1210 may have a body portion 1214 and a plurality of leg members 1212 extending from the body portion 1214. In some embodiments, the leg members 1212 can be connected to the body portion 1214 using hinges 1216 that allow the leg members 1212 to flex and/or move with respect to the body portion 1214. In particular, the leg members 1212 can pivot about the body portion 1214 and flex/move radially outwardly as the actuator 1210 moves distally. This flexing and pivoting by the leg members 1212 applies a radially outward force against the gland member 1214 and causes the aperture 350 to open.

In some embodiments, the ends of the leg members 1212 can cooperate with recesses 1224 within the gland member 1220 to secure the actuator 1210 within the valve 1200 (e.g., prevent the actuator 1210 from moving or spinning within the valve 1200) as well as aid in valve opening and closing. It is important to note that any number of leg members 1212 can be used in accordance with various embodiments of this invention. For example, the actuator 1210 may only have two leg members 1212 or the actuator can have more than two (e.g., 4 leg members 1212). Additionally or alternatively, the actuator 1210 can have a combination of flexible leg members and non-flexible members (e.g., 2 of each).

As mentioned above, the hinge 1216 allows the leg members 1212 to flex/move and pivot with respect to the body portion 1214. The hinge 1216 can be any number of elements that allow such flexion/movement and pivoting. For example, as shown in FIG. 12, the hinge 1216 may simply be a thinned area between each of the leg members 1212 and the body portion 1214 (e.g., a living hinge). Alternatively, the hinge 1216 can be a separate and distinct element that connects the leg member 1212 to the body portion 1214. For example, the hinge 1216 may be an elastomeric sleeve or elastomeric portion located between each leg member 1212 and the body portion 1214.

In some embodiments, the actuator 1210 may have an actuator channel 1218 (e.g., a flow channel) passing through the body portion 1214. When the valve 1200 is in the open mode, the actuator channel 1218 may be part of the fluid channel through the valve 1200. The actuator channel 1218 may have any shape or size opening that allows appropriate fluid flow through the actuator 1210 (e.g., circular, rectangular, oval, etc.).

Figure 13:
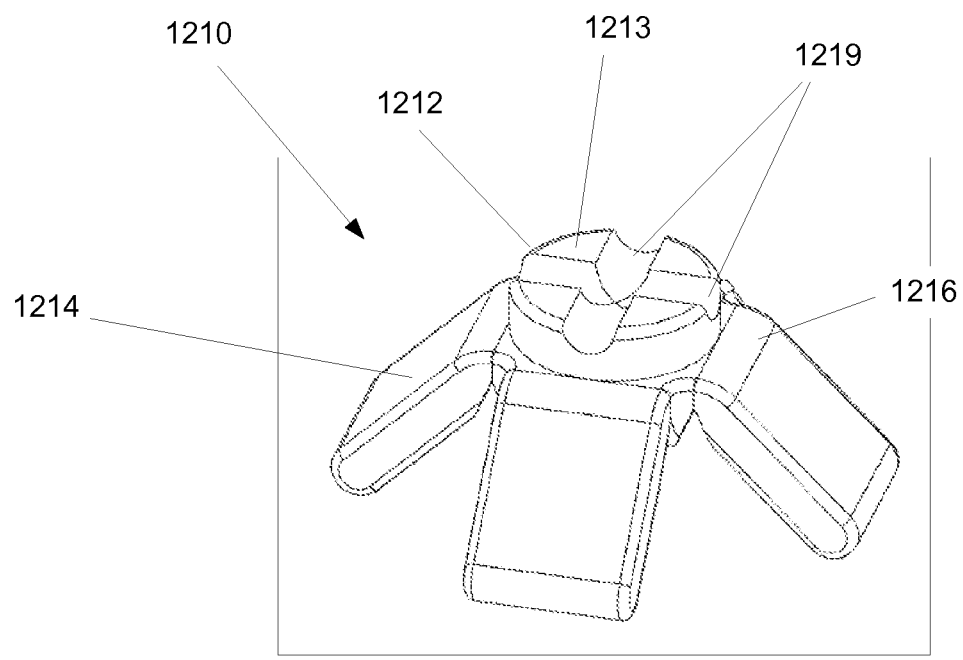
FIG. 13 schematically shows a perspective view of an alternative actuator in accordance with embodiments of the present invention.

Additionally or alternatively, as shown in FIG. 13, the actuator channel may be an indent or a groove 1219 extending along the top surface 1213 and/or outside surface of the actuator 1210. In such embodiments, as fluid is introduced into the valve 800 from the medical instrument 40, the fluid will flow within the groove/indent 1219, between the leg members 1214, through the aperture 1230 and out the outlet 120. It is also important to note, that a similar groove/indent may be used for the cannula/plug member described above.

For example, the plug member 310 may be a solid member with a groove/indent extending along the top surface and/or down the outside surface of the plug member 310. The fluid may then flow out of the medical instrument into the groove/indent, down the outside of the solid post member (e.g., within the groove/indent), and out the outlet during transfer.

Like the various embodiments described above, embodiments containing the actuator 1210 may also have the ribs 520 and relief zones 530 described above. To that end and as shown in FIG. 12, the gland member may have a distal portion 1224 (e.g., a sealing portion) that extend into the rib/relief zone area. The ribs 520 and relief zones 530 may then provide the dynamic sealing described above with respect to FIG. 10A. For example, the fluid generating the proximally directed pressure may enter the relief zones 530 and create a radially inward pressure towards the distal portion 1224 of the gland member 1220. This axial pressure will, in turn, apply a greater closing force on the aperture 1230 and increase the seal created by the aperture 1230.

It is important to note that the ribs 520 are not required to create the relief zones 530 for the embodiments described above. For example, some embodiments of the present invention may have an annular volume located around the distal portion of the resilient member 300 (e.g., between the outer diameter of the resilient member 300 and the inner diameter of the outlet housing 170) and in fluid communication with the outlet 120 of the valve. In such embodiments, the annular volume may act as the relief zone and the fluid may enter the annular volume and provide the dynamic sealing described above. Furthermore, as the valve 10 transitions from the closed mode to the open mode, portions of the resilient member 300 may deform into the annular volume and ease the transition of the valve in a manner similar to the relief zones 530 described above.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A medical valve having an open mode that permits fluid flow, and a closed mode that prevents fluid flow, the medical valve comprising:
    a housing having an inlet and an outlet;
    a rigid plug member movably mounted within the housing and having a proximal end and a distal end, the rigid plug member having a hole configured to allow fluid flow through the rigid plug member;
    a resilient member having a first seal member, the first seal member sealing the hole when the valve is in the closed mode; and
    an annular space circumscribing a portion of the resilient member having the first seal member, the annular space being configured such that a proximally directed pressure within the valve increases the seal at the hole by applying a greater force on the portion of the resilient member containing the first seal member when the valve is in the closed mode, the greater force being greater than a force applied on the portion of the resilient member when the proximally directed pressure within the valve is not present and the valve is in the closed mode.

2. A medical valve according to claim 1, wherein the housing includes a plurality of rib members extending into the annular space.

3. A medical valve according to claim 2, wherein the housing further includes a shelf portion, at least a portion of the resilient member being supported by the shelf portion and the plurality of ribs.

4. A medical valve according to claim 2, wherein the plurality of rib members divide the annular space into at least one relief zone in fluid communication with the outlet when the valve is in the closed mode.

5. A medical valve according to claim 4, wherein the resilient member deforms into the at least one relief zone as the valve transitions from the closed mode to the open mode.

6. A medical valve according to claim 4, wherein the hole is aligned with the relief zone when the valve is in the open mode.

7. A medical valve according to claim 4, wherein the at least one relief zone is configured to redirect the proximally directed pressure within the valve to apply a radial force on the first seal member.

8. A medical valve according to claim 7, wherein the radial force applied on the first seal member is greater than a force applied to a remainder portion of the resilient member by the proximally directed pressure.

9. A medical valve according to claim 1, wherein the force applied on the portion of the resilient member containing the first seal member increases with the proximally directed pressure.

10. A medical valve according to claim 1, wherein the annular space is at least partially defined by at least a portion of the housing.

11. A medical valve according to claim 1 further comprising:
    a second seal member located proximal to the hole when the valve is in the closed mode, the first seal member being located distal to the hole when the valve is in the closed mode.

12. A medical valve according to claim 11, wherein the first and second seal members are o-rings.

13. A medical valve according to claim 11, wherein the first and second seal members are integral to the resilient member.

14. A medical valve according to claim 1, further comprising a plurality of guide posts at the outlet of the valve, the guide posts centering the rigid plug member within the outlet as the rigid plug member moves distally.

15. A medical valve according to claim 1, wherein the rigid plug member has two or more holes between its proximal and distal end, the seal member sealing the two or more holes when the valve is in the closed mode.

16. A medical valve according to claim 1, wherein the rigid plug member is a cannula.

17. A medical valve according to claim 1, wherein the first seal member is a ring seal extending from a first location distal to the hole to a second location proximal to the hole, the ring seal providing a constant seal along its length against the rigid plug member when the valve is in the closed mode.

18. A medical valve according to claim 1, wherein the resilient member deforms into the annular space as the valve transitions from the closed mode to the open mode.

19. A medical valve according to claim 1, wherein the annular space is configured to redirect the proximally directed pressure within the valve to apply a radial force on the first seal member.

* * * * *